US010377991B2

(12) United States Patent
Gotoh et al.

(10) Patent No.: US 10,377,991 B2
(45) Date of Patent: Aug. 13, 2019

(54) METHOD OF PRODUCING AIRWAY EPITHELIAL CELLS

(71) Applicant: KYOTO UNIVERSITY, Kyoto (JP)

(72) Inventors: Shimpei Gotoh, Kyoto (JP); Yuki Yamamoto, Kyoto (JP); Satoshi Konishi, Kyoto (JP); Michiaki Mishima, Kyoto (JP)

(73) Assignee: KYOTO UNIVERSITY, Kyoto (JP)

(*) Notice: Subject to any disclaimer, the term of this patent is extended or adjusted under 35 U.S.C. 154(b) by 49 days.

(21) Appl. No.: 15/558,670

(22) PCT Filed: Mar. 18, 2016

(86) PCT No.: PCT/JP2016/059786

§ 371 (c)(1),
(2) Date: Sep. 15, 2017

(87) PCT Pub. No.: WO2016/148307

PCT Pub. Date: Sep. 22, 2016

(65) Prior Publication Data

US 2018/0112186 A1 Apr. 26, 2018

(30) Foreign Application Priority Data

Mar. 19, 2015 (JP) ................................ 2015-056791

(51) Int. Cl.
*C12N 5/00* (2006.01)
*C12N 5/071* (2010.01)

(52) U.S. Cl.
CPC ........ *C12N 5/0688* (2013.01); *C12N 2500/38* (2013.01); *C12N 2501/11* (2013.01); *C12N 2501/119* (2013.01); *C12N 2501/148* (2013.01); *C12N 2501/155* (2013.01); *C12N 2501/16* (2013.01); *C12N 2501/727* (2013.01); *C12N 2501/73* (2013.01); *C12N 2501/999* (2013.01); *C12N 2506/45* (2013.01)

(58) Field of Classification Search
USPC .......................................................... 435/325
See application file for complete search history.

(56) References Cited

U.S. PATENT DOCUMENTS

| | | | |
|---|---|---|---|
| 9,453,205 B2 * | 9/2016 | Ahlfors ................ | C12N 5/0623 |
| 2016/0068816 A1 | 3/2016 | Osafune et al. | |

FOREIGN PATENT DOCUMENTS

| | | |
|---|---|---|
| EP | 3266864 | 1/2018 |
| WO | 2014/168264 A1 | 10/2014 |
| WO | 2016/143803 | 9/2016 |

OTHER PUBLICATIONS

Pulmonary alveolar cells, Wikipedia, 2019.*
Crystal (Proc. Am. Thorac. Soc., 2008, vol. 5, No. 7, p. 772-777).*
Da Gramont (Oncoimmunol., 2017, vol. 6, No. 1, e1257453).*
Da Gramont (Oncoimmunol., 2017, vol. 6, No. 1, e1257453) taught TGFFβinhibitors. Hopkins (Expert Opin. Therapeutic Patents, 2016, vol. 26, No. 10, p. 1115-1128.*
Satoshi Konishi et al, "Directed Induction of Functional Multi-ciliated Cells in Proximal Airway Epithelial Spheroids from Human Pluripotent Stem Cells", Stem Cell Reports, Jan. 1, 2016, pp. 18-25, vol. 6, No. 1.
Supplemental European Search Report issued in connection with the corresponding European application No. 16765134.8, dated Aug. 3, 2018.
Rippon, H. J. et al, "Initial Observations on the Effect of Medium Composition on the Differentiation of Murine Embryonic Stem Cells to Alveolar Type II Cells", Cloning Stem Cells, 2004, pp. 49-56, vol. 6, No. 2.
Coraux, C. et al, "Embryonic Stem Cells Generate Airway Epithelial Tissue", Am. J. Respir. Cell Mol. Biol., 2005, pp. 87-92, vol. 32.
Morrisey, E. E. and Hogan, B. L. M., "Preparing for the First Breath: Genetic and Cellular Mechanisms in Lung Development", Dev. Cell., Jan. 19, 2010, pp. 8-23, vol. 18(1).
Ghaedi, M. et al., "Human iPS cell-derived alveolar epithelium repopulates lung extracellular matrix", J. Clin. Invest., 2013, pp. 4950-4962, vol. 123(11).
Huang, S. X. et al., Nat. Biotechnol., "Efficient generation of lung and airway epithelial cells from human pluripotent stem cells", Jan. 2014, pp. 84-91, vol. 32(1).
Gotoh, S. et al., "Generation of Alveolar Epithelial Spheroids via Isolated Progenitor Cells from Human Pluripotent Stem Cells", Stem Cell Reports, Sep. 9, 2014, pp. 394-403, vol. 3.
Rippon, H. J. et al, Cloning Stem Cells 6: 49-56, 2004.
Coraux, C. et al, Am. J. Respir. Cell Mol. Biol., 32:87-92, 2005.
Morrisey, E. E. and Hogan, B. L. M., Dev. Cell., 18: 8-23, 2010.
Ghaedi, M. et al., J. Clin. Invest., vol. 123, pp. 4950-4962, 2013.
Huang, S. X. et al., Nat. Biotechnol., vol. 32, pp. 84-91, 2014.
Gotoh, S. et al., Stem Cell Reports, vol. 3, pp. 394-403, 2014.
Kubo A. et al., "Sentan: A Novel Speci?c Component of the Apical Structure of Vertebrate Motile Cilia", Molecular Biology of the Cell, 2008, vol. 19, pp. 5338-5346.
You Y. et al., "Role of f-box factor foxj1 in differentiation of ciliated airway epithelial cells", Am J Physiol Lung Cell Mol Physiol., 2004, vol. 286,. pp. L650-L657.
Hornef N. et al., "DNAH5 Mutations Are a Common Cause of Primary Ciliary Dyskinesia with Outer Dynein Arm Defects", Am J Respir Crit Care Med., 2006, vol. 174, pp. 120-126.
Wikipedia, "3D cell culture", printed May 1, 2019, online publication, https://en.wikipedia.org/wiki/3D_cell_culture, (7 pages).
Kubo A. et al., "Sentan: A Novel Specific Component of the Apical Structure of Vertebrate Motile Cilia", Molecular Biology of the Cell, 2008, vol. 19, pp. 5338-5346.

* cited by examiner

*Primary Examiner* — Michael C Wilson
(74) *Attorney, Agent, or Firm* — Lucas & Mercanti, LLP

(57) ABSTRACT

This invention provides a method for stably producing airway epithelial cells from pluripotent stem cells. Specifically, the invention relates to a method for producing airway epithelial cells from pluripotent stem cells comprising steps: (1) culturing pluripotent stem cells in a medium containing activin A and a GSK3β inhibitor; (2) culturing the cells obtained in Step (1) in a medium containing a BMP inhibitor and a TGFβ inhibitor; (3) culturing the cells obtained in Step (2) in a medium containing BMP4, retinoic acid, and a GSK3β inhibitor; (5) subjecting the cells obtained after Step (3) to three-dimensional culture in a medium containing a GSK3β inhibitor, FGF10, and a ROCK inhibitor; and (6) subjecting the proximal airway epithelial progenitor cells obtained in Step (5) to three-dimensional culture in a medium containing a ROCK inhibitor.

10 Claims, 10 Drawing Sheets
(7 of 10 Drawing Sheet(s) Filed in Color)

Fig. 2A-B
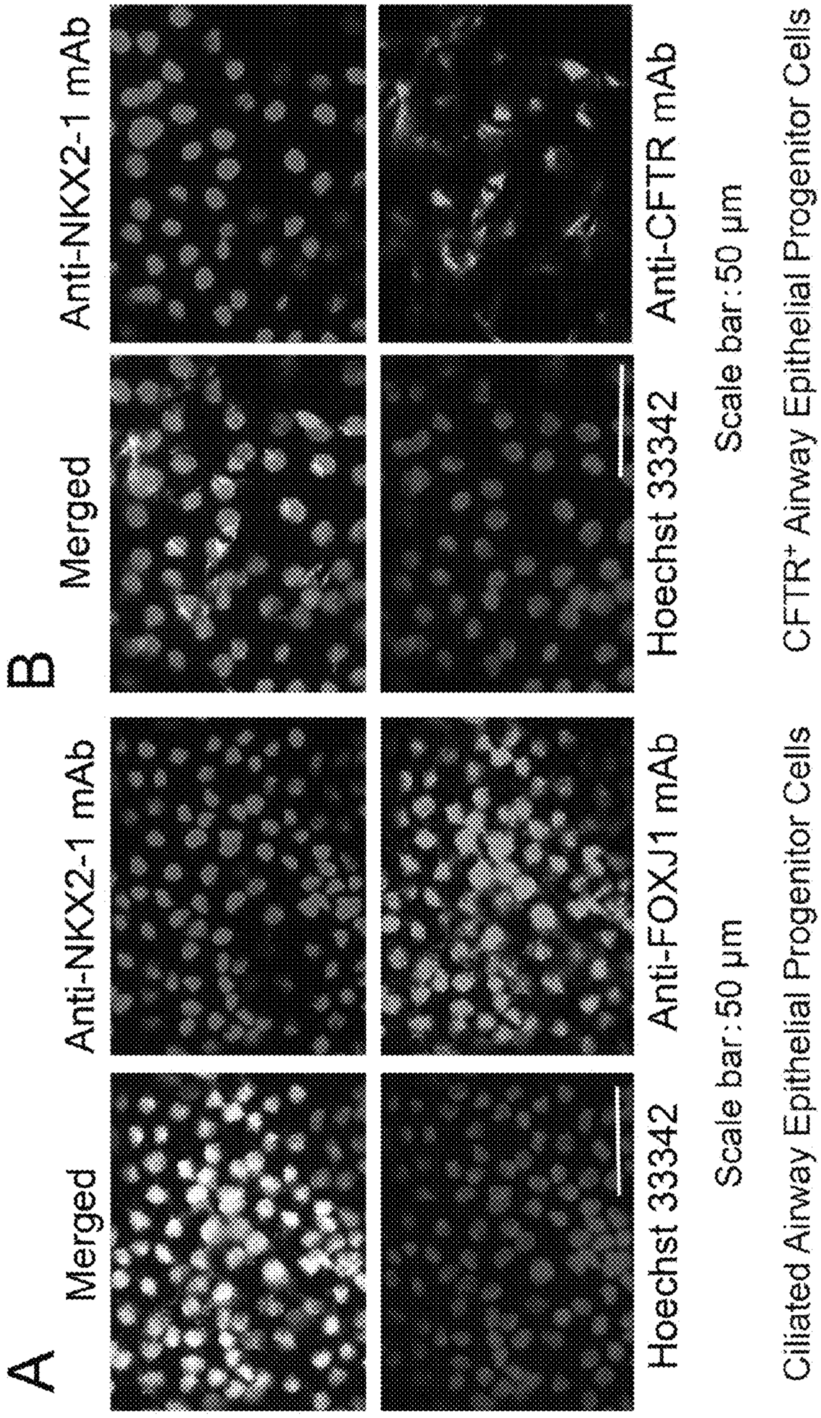

Fig. 2C-D
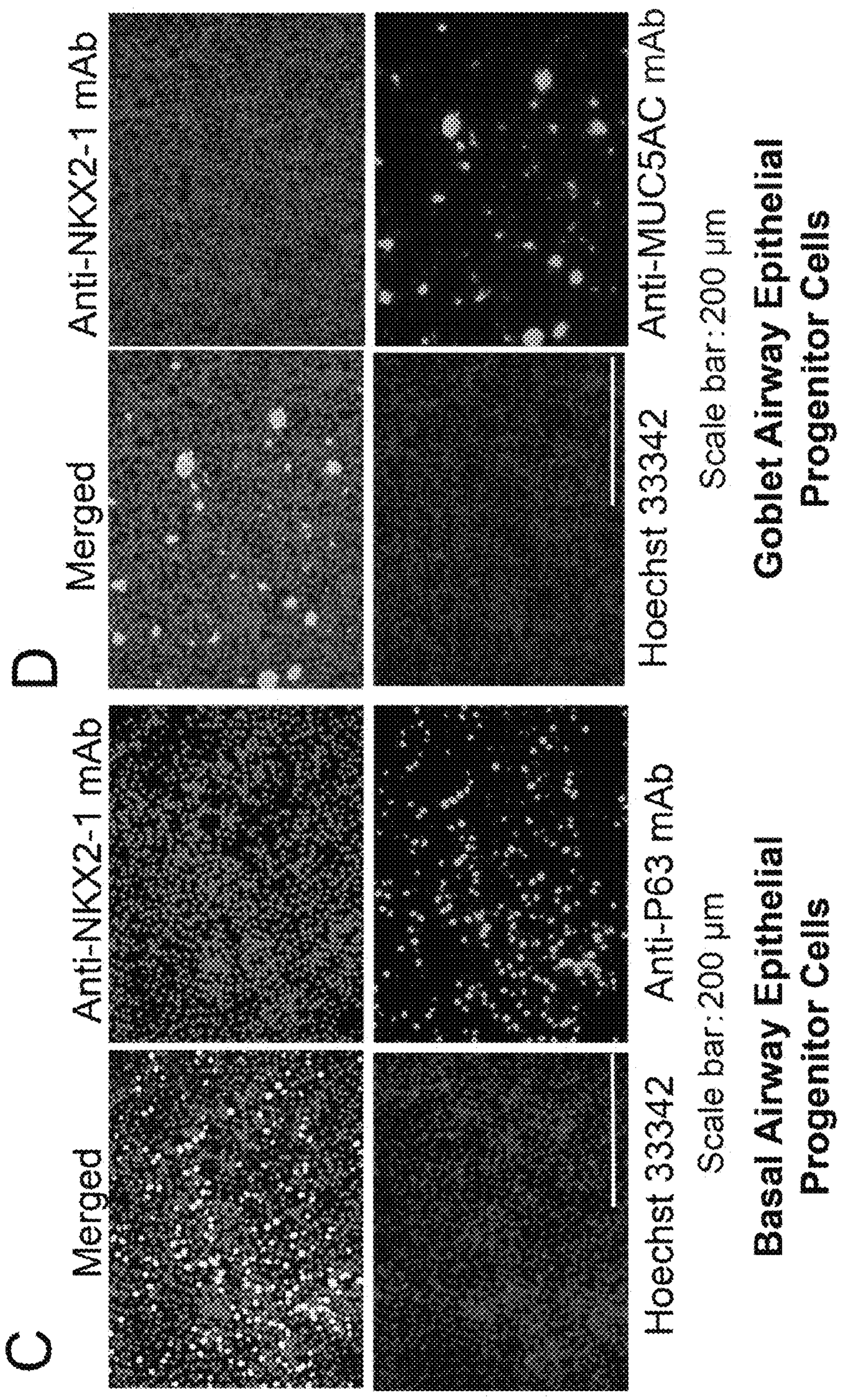

METHOD OF PRODUCING AIRWAY EPITHELIAL CELLS

CROSS-REFERENCE TO RELATED APPLICATIONS

This application is a 371 of PCT/JP2016/059786, filed Mar. 18, 2016, which claims the benefit of Japanese Patent Application No. 2015-056791, filed Mar. 19, 2015.

TECHNICAL FIELD

The present invention relates to a method for producing airway epithelial cells from pluripotent stem cells and a kit for producing airway epithelial cells from pluripotent stem cells, for example.

BACKGROUND ART

In recent years, cells having pluripotency, such as embryonic stem cells (ES cells) or induced pluripotent stem cells (iPS cells) obtained by introducing undifferentiated-cell-specific genes into somatic cells, have been reported, methods for inducing cells in the respiratory system, such as alveolar epithelial cells, from such cells have been reported (WO 2014/168264; Rippon, H. J. et al, Cloning Stem Cells 6: 49-56, 2004; Coraux, C. et al, Am. J. Respir. Cell Mol. Biol., 32: 87-92, 2005; Morrisey, E. E. and Hogan, B. L. M., Dev. Cell., 18: 8-23, 2010; Ghaedi, M. et al., J. Clin. Invest., Vol. 123, pp. 4950-62, 2013; Huang, S. X. et al., Nat. Biotechnol., Vol. 32, pp. 84-91, 2014; and Gotoh, S. et al., Stem Cell Reports, Vol. 3, pp. 394-403, 2014), and growth factors and the like that are necessary for the induction of such cells have also been reported. The present inventors discloses that three-dimensional coculture of human pluripotent stem cells is useful for induction of differentiation into type II alveolar epithelial cells and a reporter enables isolation of type II alveolar epithelial cells (Gotoh, S. et al., Stem Cell Reports, Vol. 3, pp. 394-403, 2014). The present inventors also disclose a method for producing alveolar epithelial progenitor cells from pluripotent stem cells (WO 2014/168264).

To date, elucidation of pathological conditions of airway diseases causing ciliary motility disorders or mucociliary clearance abnormalities and development of therapeutic agents for the airway diseases have been desired. Elucidation of pathological conditions and development of therapeutic agents as described above involve the use of airway epithelial cells, such as ciliated airway epithelial cells, as target cells. As with the case of the alveolar epithelial cells described above, however, there have been no reports concerning induction of airway epithelial cells from human pluripotent stem cells in the past.

SUMMARY OF THE INVENTION

It is an object of the present invention to provide a method for producing airway epithelial cells from pluripotent stem cells and a kit for producing airway epithelial cells from pluripotent stem cells.

The present inventors have conducted concentrated studies in order to attain the above objects. As a result, they discovered that pluripotent stem cells could be induced to differentiate into airway epithelial cells with the use of various growth factors and compounds. This has led to the completion of the present invention.

Specifically, the present invention includes the following.

[1] A method for producing airway epithelial cells from pluripotent stem cells comprising Steps (1) to (3), (5), and (6) below:

(1) culturing pluripotent stem cells in a medium containing activin A and a GSK3β inhibitor;

(2) culturing the cells obtained in Step (1) in a medium containing a BMP inhibitor and a TGFβ inhibitor;

(3) culturing the cells obtained in Step (2) in a medium containing BMP4, retinoic acid, and a GSK3β inhibitor;

(5) subjecting the cells obtained after Step (3) to three-dimensional culture in a medium containing a GSK3β inhibitor, FGF10, and a ROCK inhibitor; and (6) subjecting the proximal airway epithelial progenitor cells obtained in Step (5) to three-dimensional culture in a medium containing a ROCK inhibitor.

[2] The method according to [1], wherein the airway epithelial cells are selected from the group consisting of ciliated airway epithelial cells, airway mucin-producing cells, basal airway epithelial cells, and Club cells.

[3] The method according to [1] or [2], which further comprises, following Step (3), the Step (4) culturing the obtained ventral anterior foregut cells in a medium containing a GSK3β inhibitor and FGF10 to induce the cells to differentiate into airway epithelial progenitor cells.

[4] The method according to any one of [1] to [3], wherein the GSK3β inhibitor is CHIR99021, the BMP inhibitor is Noggin, the TGFβ inhibitor is SB431542, and the ROCK inhibitor is Y-27632.

[5] The method according to any one of [1] to [4], wherein Step (1) comprises culturing pluripotent stem cells in a medium further supplemented with a ROCK inhibitor and/or an HDAC inhibitor.

[6] The method according to [5], wherein the ROCK inhibitor is Y-27632 and/or the HDAC inhibitor is sodium butyrate.

[7] The method according to any one of [1] to [6], which further comprises, following Step (3), a step of isolating CPM-positive cells as ventral anterior foregut cells.

[8] The method according to any one of [3] to [7], wherein Step (4) comprises subjecting ventral anterior foregut cells to culture in a medium further supplemented with a ROCK inhibitor.

[9] The method according to [8], wherein the ROCK inhibitor is Y-27632.

[10] The method according to any one of [1] to [9], wherein, in Step (6), proximal airway epithelial progenitor cells are subjected to three-dimensional culture in a medium further supplemented with a NOTCH signal inhibitor and the resulting airway epithelial cells are ciliated airway epithelial cells.

[11] The method according to [10], wherein the NOTCH signal inhibitor is DAPT.

[12] The method according to any one of [1] to [11], which further comprises, following Step (6), a step of isolating cells positive for one or more ciliated airway epithelial cell markers selected from the group consisting of Sentan (SNTN), FOXJ1, and DNAHS as ciliated airway epithelial cells.

[13] A kit for producing airway epithelial cells from pluripotent stem cells comprising activin A, a GSK3β inhibitor, a BMP inhibitor, a TGFβ inhibitor, BMP4, retinoic acid, FGF10, and a ROCK inhibitor.

[14] The kit according to [13], wherein the airway epithelial cells are selected from the group consisting of ciliated airway epithelial cells, airway mucin-producing cells, basal airway epithelial cells, and Club cells.

[15] The kit according to [13] or [14], wherein the GSK3β inhibitor is CHIR99021, the BMP inhibitor is Noggin, the TGFβ inhibitor is SB431542, and the ROCK inhibitor is Y-27632.

[16] The kit according to any one of [13] to [15], which further comprises an HDAC inhibitor.

[17] The kit according to [16], wherein the HDAC inhibitor is sodium butyrate.

[18] The kit according to any one of [13] to [17], which further comprises a NOTCH signal inhibitor, and wherein the airway epithelial cells are ciliated airway epithelial cells.

[19] The kit according to [18], wherein the NOTCH signal inhibitor is DAPT.

This description includes part or all of the content as disclosed in Japanese Patent Application No. 2015-056791, which is a priority document of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A and 2B show double fluorescent immunostaining images of airway epithelial progenitor cells on Day 28 (i.e., upon completion of Step 4) induced to differentiate with the use of human iPS cells (201B7).

FIGS. 2C and 2D are continued from FIGS. 2A and 2B.

EMBODIMENTS FOR CARRYING OUT THE INVENTION

Figure 1:
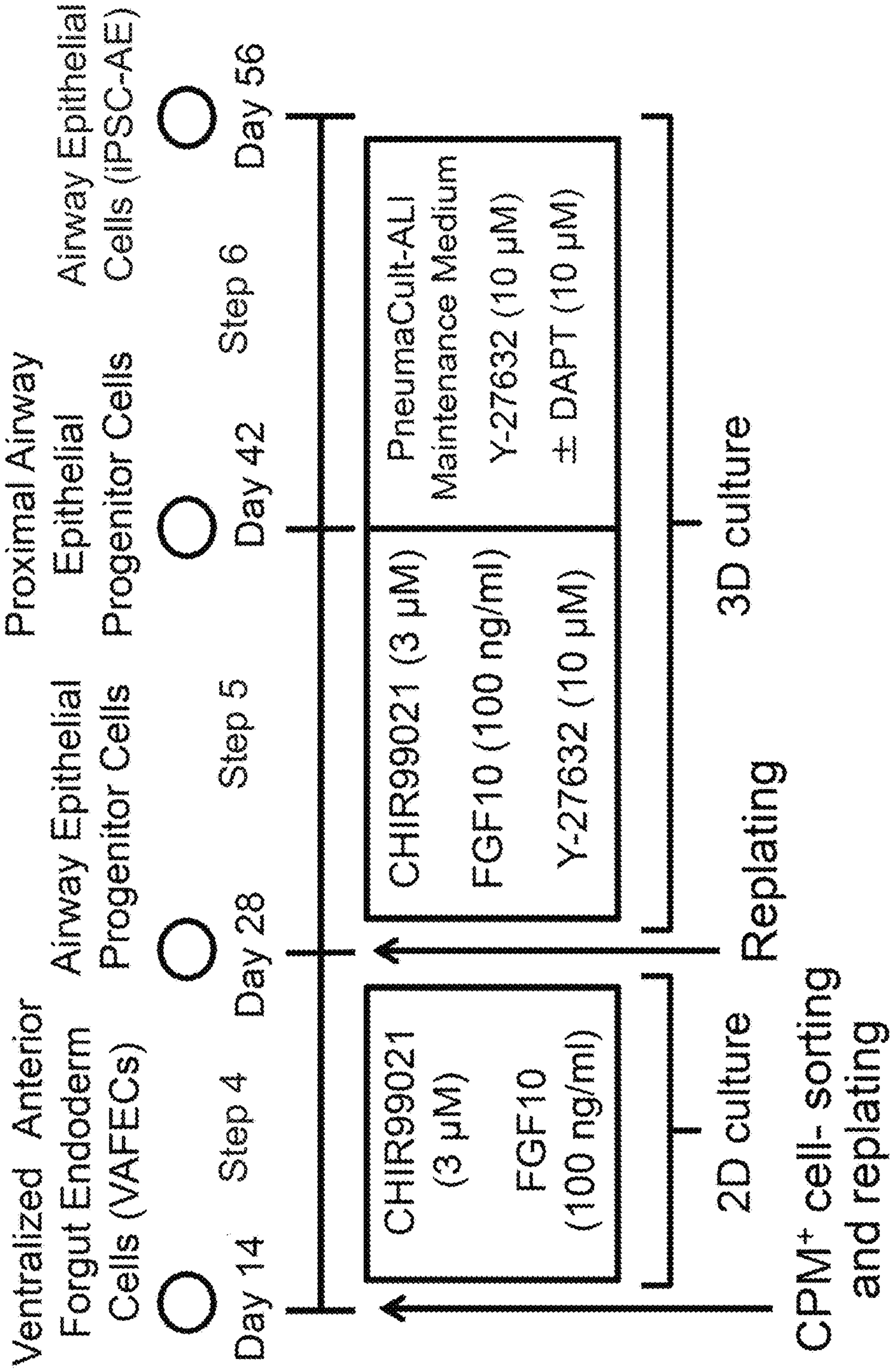
FIG. 1 shows a method for inducing airway epithelial cells from ventral anterior foregut cells using human pluripotent stem cells.

[Method for Producing Airway Epithelial Cells from Pluripotent Stem Cells]

The method for producing airway epithelial cells from pluripotent stem cells according to the present invention comprises Steps (1) to (3), (5), and (6) below:

(1) culturing pluripotent stem cells in a medium containing activin A and a GSK3β inhibitor;

(2) culturing the cells obtained in Step (1) in a medium containing a BMP inhibitor and a TGFβ inhibitor;

(3) culturing the cells obtained in Step (2) in a medium containing BMP4, retinoic acid, and a GSK3β inhibitor;

(5) subjecting the cells obtained after Step (3) to three-dimensional culture in a medium containing a GSK3β inhibitor, FGF10, and a ROCK inhibitor; and (6) subjecting the proximal airway epithelial progenitor cells obtained in Step (5) to three-dimensional culture in a medium containing a ROCK inhibitor.

The method for producing airway epithelial cells from pluripotent stem cells according to the present invention may further comprise, following Step (3), the Step (4) culturing the obtained ventral anterior foregut cells in a medium containing a GSK3β inhibitor and FGF10 to induce the cells to differentiate into airway epithelial progenitor cells.

In the present invention, the term "ventral anterior foregut cells" refers to cells that are destined to differentiate into the thyroid gland or lung in the presence of developmentally appropriate stimuli, and such cells express NKX2-1 (NKX2.1), GATA6, and/or HOPX.

In the present invention, the term "airway epithelial progenitor cells" refers to cells that are destined to differentiate into ciliated airway epithelial cells, CFTR-positive airway epithelial cells, airway mucin-producing cells, basal airway epithelial cells, neuroendocrine epithelial cells, Club cells, or alveolar epithelial cells in the presence of developmentally appropriate stimuli, and such cells express FOXJ1, CFTR, P63, MUCSAC, and/or NKX2-1.

In the present invention, the term "proximal airway epithelial progenitor cells" refers to ciliated airway epithelial cells, airway mucin-producing cells, basal airway epithelial cells, neuroendocrine epithelial cells, or Club cells, and such cells express SOX2 and NKX2-1.

In the present invention, the term "airway epithelial cells" refers to epithelial cells existing in the proximal airway and in the distal airway in the lung, and representative examples thereof include ciliated airway epithelial cells, Club cells, basal airway epithelial cells, airway mucin-producing cells, CFTR-positive epithelial cells, and neuroendocrine cells.

In the present invention, the term "ciliated airway epithelial cells" refers to epithelial cells comprising many dynamic cilia per cell in a histological sense, and the term refers to epithelial cells comprising cilia classified as a "9+2" arrangement in a morphological sense. Such cells express Sentan (SNTN), acetylated tubulin, FOXJ1, DNAH5, and/or NKX2-1.

In the present invention, the term "Club cells" refers to epithelial cells that produce cell-specific proteins, such as SCGB3A2, including SCGB1A1, as with the Club cells existing in large quantities in the distal airway in the lung.

In the present invention, the term "basal airway epithelial cells" refers to epithelial cells that produce cell-specific proteins, such as NGFR and p63, including KRT5, as with basal cells existing in large quantities in areas ranging from the proximal airway to the distal airway in the lung.

In the present invention, the term "airway mucin-producing cells" refers to epithelial cells that produce cell-specific proteins, such as AGR2 and SPDEF, including MUC5AC, as with goblet cells existing in large quantities in areas ranging from the proximal airway to the distal airway in the lung.

The steps of the method for producing airway epithelial cells from pluripotent stem cells according to the present invention are described below.

(1) Step of Culture in a Medium Containing Activin A and a GSK3β Inhibitor (Step 1)

A medium used in the step of pluripotent stem cell culture according to the present invention can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, Glutamax (Invitrogen), nonessential amino acids, vitamins, growth factors, low-molecular-weight compounds, antibiotics, antioxidants, pyruvic acids, buffer agents, and inorganic salts. RPMI 1640 medium supplemented with B27 and antibiotics is preferable.

In this step, pluripotent stem cells are cultured in a medium prepared by supplementing the basal medium described above with activin A and a GSK3β inhibitor. In this step, an HDAC inhibitor may further be added.

Activin A is a homodimer with two beta A chains, the amino acid sequence of activin A is 100% homologous to that of a protein of a human, mouse, rat, pig, cow, or cat, and, accordingly, relevant species are not particularly limited. In the present invention, activin A is preferably of an active form with the N-terminal peptide being cleaved, and it is preferably a homodimer comprising, bound thereto via a disulfide bond, the Gly311-Ser426 fragment with the N-terminal peptide of the inhibin beta A chain (e.g., NCBI Accession Number NP_002183) being cleaved. Such activin A is commercially available from, for example, Wako and R&D Systems.

The activin A concentration in a medium is, for example, 10 ng/ml to 1 mg/ml, and it is specifically 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 150 ng/ml, 200 ng/ml, 300 ng/ml, 400 ng/ml, 500 ng/ml, 600 ng/ml, 700 ng/ml, 800 ng/ml, 900 ng/ml, or 1 mg/ml, although the concentration is not limited thereto. The concentration is preferably 100 ng/ml.

The term "GSK3β inhibitor" used herein is defined as a substance that inhibits kinase activity of the GSK-3β protein (e.g., the capacity for phosphorylation of β-catenin), and many such substances are already known. Examples thereof include: an indirubin derivative, such as BIO, which is also known as a GSK-3β inhibitor IX (6-bromoindirubin-3'-oxime); a maleimide derivative, such as SB216763 (3-(2,4-dichlorophenyl)-4-(1-methyl-1H-indol-3-yl)-1H-pyrrole-2,5-dione); a phenyl α-bromomethylketone compound, such as a GSK-3β inhibitor VII (4-dibromoacetophenone); a cell-permeable phosphorylated peptide, such as L803-mts, which is also known as a GSK-3β peptide inhibitor (i.e., Myr-N-GKEAPPAPPQSpP-$NH_2$); and CHIR99021, such as 6-[2-[4-(2,4-dichlorophenyl)-5-(4-methyl-1H-imidazol-2-yl)pyrimidin-2-ylamino]-ethylamino]pyridine-3-carbonitrile, with high selectivity. While such compounds are commercially available from, for example, Calbiochem or Biomol, and easily used, such compounds may be obtained from other companies, or persons may prepare such compounds by themselves.

A GSK-3βinhibitor that can be preferably used in the present invention is CHIR99021. In this step, the CHIR99021 concentration in a medium is, for example, 1 nM to 50 μM, and it is specifically 1 nM, 10 nM, 50 nM, 100 nM, 500 nM, 750 nM, 1 μM, 1.5 μM, 2 μM, 2.5 μM, 3 μM, 3.5 μM, 4 μM, 4.5 μM, 5 μM, 6 μM, 7 μM, 8 μM, 9 μM, 10 μM, 15 μM, 20 μM, 25 μM, 30 μM, 40 μM, or 50 μM, although the concentration is not limited thereto. In this step, the concentration is preferably 1 μM.

The term "HDAC inhibitor" is defined as a substance that inhibits or inactivates enzyme activity of histone deacetylase (HDAC). Examples thereof include: low-molecular-weight inhibitors, such as valproic acid (VPA) (Nat. Biotechnol., 26 (7): 795-797, 2008), trichostatin A, sodium butyrate (NaB), MC 1293, and M344; nucleic acid-based expression inhibitors, such as siRNAs and shRNAs against HDAC (e.g., HDAC1 siRNA Smartpool® (Millipore) and HuSH 29mer shRNA Constructs against HDAC1 (OriGene)); and DNA methyltransferase inhibitors (e.g., 5'-azacytidine) (Nat. Biotechnol., 26 (7): 795-797, 2008).

An HDAC inhibitor that can be preferably used in the present invention is sodium butyrate (NaB). The sodium butyrate (NaB) concentration in a medium is, for example, 1 μM to 5 mM, and it is specifically 1 μM, 10 μM, 50 μM, 100 μM, 125 μM, 250 μM, 500 μM, 750 μM, 1 mM, 2 mM, 3 mM, 4 mM, or 5 mM, although the concentration is not limited thereto. The concentration is preferably 125 μM to 250 μM.

In this step, culture may be conducted in a culture vessel treated with a coating agent. A coating agent may be a naturally occurring or artificially synthesized extracellular matrix. Examples thereof include BD Matrigel, collagen, gelatin, laminin, heparan sulfate proteoglycan, entactin, and a combination of any thereof, with Matrigel being preferable.

This step may comprise a process of pluripotent stem cell detachment. Examples of methods for cell detachment include a method of mechanical detachment and a method of cell detachment involving the use of a cell detachment solution having protease activity and collagenase activity (e.g., Accutase™ and Accumax™ or a cell detachment solution having collagenase activity alone. It is preferable that human pluripotent stem cells be detached with the use of a cell detachment solution having protease activity and collagenase activity, with the use of Accutase™ being particularly preferable.

When the step comprises a process of cell detachment, a ROCK inhibitor may be added to a medium, so as to inhibit pluripotent stem cell death caused by detachment.

An ROCK inhibitor is not particularly limited, provided that it can inhibit functions of Rho kinase (ROCK). Examples thereof include: Y-27632 ((+)-(R)-trans-4-(1-aminoethyl)-N-(4-pyridyl)cyclohexanecarboxamide dihydrochloride) (e.g., Ishizaki et al., Mol. Pharmacol., 57, 976-983, 2000; Narumiya et al., Methods Enzymol., 325, 273-284, 2000); Fasudil/HA1077 (e.g., Uenata et al., Nature 389: 990-994, 1997); H-1152 (e.g., Sasaki et al., Pharmacol. Ther., 93: 225-232, 2002); Wf-536 (e.g., Nakajima et al., Cancer Chemother. Pharmacol., 52 (4): 319-324, 2003) and derivatives thereof; antisense nucleic acids against ROCK; RNA interference-inducible nucleic acids (e.g., siRNA); dominant-negative variants; and expression vectors thereof. Since other low-molecular-weight compounds are known as ROCK inhibitors, such compounds and derivatives thereof can also be used in the present invention (e.g., U.S. Patent Application Publication Nos. 2005/0209261, 2005/0192304, 2004/0014755, 2004/0002508, 2004/0002507, 2003/0125344, and 2003/0087919, WO 2003/062227, WO 2003/059913, WO 2003/062225, WO 2002/076976, and WO 2004/039796). In the present invention, one or more types of ROCK inhibitors can be used.

An ROCK inhibitor that can be preferably used in the present invention is Y-27632. The Y-27632 concentration is, for example, 100 nM to 50 μM, and it is specifically 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, or 50 μM, although the concentration is not limited thereto. The concentration is preferably 10 μM.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period is at least 3 days, 4 days, 5 days, 6 days, 7 days, 8 days, 9 days, 10 days, 11 days, or 12 days. The culture period is preferably at least 6 days, and it is particularly preferably 6 days. When the ROCK inhibitor is added, the duration of addition is 1 day or 2 days, and preferably 2 days. When the HDAC inhibitor is further added, such addition is initiated on the day following the initiation of the step, and culture is conducted for at least 3 days, 4 days, 5 days, 6 days, 7 days, 8 days, 9 days, 10 days, or 11 days. Culture is preferably conducted for at least 5 days, and particularly preferably for 5 days, in the presence of the HDAC inhibitor.

(2) Step of Culture in a Medium Containing a BMP Inhibitor and a TGFβ Inhibitor (Step 2)

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, Glutamax (Invitrogen), nonessential amino acids, vitamins, growth factors, low-molecular-weight compounds, antibiotics, antioxidants, pyruvic acids, buffer agents, and inorganic salts. A medium mixture of DMEM and Ham's F12 supplemented with Glutamax, B27, N2, 3'-thiol glycerol, and ascorbic acid is preferable.

In this step, the cells obtained in the previous step (i.e., the step of pluripotent stem cell culture in a medium containing activin A and a GSK3β inhibitor) are cultured in a medium prepared by supplementing the basal medium with a BMP inhibitor and a TGFβ inhibitor.

Examples of BMP inhibitors include: protein-based inhibitors, such as Chordin, Noggin, and Follistatin; dorsomorphin (i.e., 6-[4-(2-piperidin-1-yl-ethoxy)phenyl]-3-pyridin-4-yl-pyrazolo[1,5-a]pyrimidine) and a derivative thereof (P. B. Yu et al., 2007, Circulation, 116: II_60; P. B. Yu et al., 2008, Nat. Chem. Biol., 4: 33-41; J. Hao et al., 2008, PLoS ONE, 3 (8): e2904); and LDN-193189 (i.e., 4-(6-(4-(piperazin- 1-yl)phenyl)pyrazolo [1,5- a]pyrimidin-3 -yl)quinoline). Dorsomorphin and LDN-193189 are commercially available from Sigma-Aldrich and Stemgent, respectively.

A BMP inhibitor that can be preferably used in the present invention is Noggin. The Noggin concentration in a medium is not particularly limited, provided that BMP can be inhibited. For example, such concentration is 1 ng/ml to 2 μg/ml, and it is specifically 1 ng/ml, 10 ng/ml, 50 ng/ml, 100 ng/ml, 200 ng/ml, 300 ng/ml, 400 ng/ml, 500 ng/ml, 600 ng/ml, 700 ng/ml, 800 ng/ml, 900 ng/ml, 1 μg/ml, or 2 μg/ml. The concentration is preferably 100 ng/ml.

The term "TGFβ inhibitor" used herein refers to a substance that inhibits signal transmission from the binding of TGFβ to a receptor leading to SMAD. A TGFβ inhibitor is not particularly limited, provided that such substance inhibits TGFβ from binding to a receptor; i.e., the ALK family, or such substance inhibits phosphorylation of SMAD caused by the ALK family. Examples thereof include Lefty-1 (e.g., NCBI Accession Nos. mouse NM_010094 and human NM_020997), SB431542 (4-(4-(benzo[d] [1,3]dioxol-5-yl)-5-(pyridin-2-yl)- 1H-imidazol-2-yl)benzamide), SB202190 (R. K. Lindemann et al., Mol. Cancer, 2003, 2: 20), SB505124 (GlaxoSmithKline), NPC30345, SD093, SD908, SD208 (Scios), LY2109761, LY364947, LY580276 (Lilly Research Laboratories), A-83-01 (WO 2009/146408), and derivatives thereof.

A TGFβ inhibitor that can be preferably used in the present invention is SB431542. The SB431542 concentration in a medium is not particularly limited, provided that TGFβ is inhibited. For example, such concentration is 1μM to 500 μM, and it is specifically 1 μM, 2 μM, 3 μM, 4 μM, 5 μM, 6 μM, 7 μM, 8 μM, 9 μM, 10 μM, 15 μM, 20 μM, 25 μM, 30 μM, 35 μM, 40 μM, 45 μM, 50 μM, 60 μM, 70 μM, 80 μM, 90 μM, 100 μM, 200 μM, 300 μM, 400 μM, or 500 μM. The concentration is preferably 10 μm.

In this step, culture may be conducted in a culture vessel treated with a coating agent. Examples of coating agents include BD Matrigel, collagen, gelatin, laminin, heparan sulfate proteoglycan, entactin, and a combination of any thereof, with Matrigel being preferable.

This step may be implemented by exchanging the cell culture medium obtained in the previous step (a culture solution) with the medium described above (a culture solution). Alternatively, cells may be detached and reseeded in a culture vessel. When cells are to be detached, particular cells may be selected, and, for example, SOX17- and/or FOXA2-positive cells may be selected and used in this step. This method is preferably implemented by means of media exchange.

When the step comprises a process of cell detachment, a ROCK inhibitor may be added to a culture solution, so as to inhibit pluripotent stem cell death caused by detachment.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period is at least 1 day, 2 days, 3 days, 4 days, 5 days, 6 days, 7 days, or 8 days. The culture period is preferably 4 days.

(3) Step of Culture in a Medium Containing BMP4, Retinoic Acid, and a GSK3β Inhibitor (Step 3)

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, Glutamax (Invitrogen), nonessential amino acids, vitamins, growth factors, low-molecular-weight compounds, antibiotics, antioxidants, pyruvic acids, buffer agents, and inorganic salts. A medium mixture of DMEM and Ham's F12 supplemented with Glutamax, B27, N2, 3'-thiol glycerol, and ascorbic acid is preferable.

In this step, the cells obtained in the previous step (i.e., the step of culture in a medium containing a BMP inhibitor and a TGFβ inhibitor) are cultured in a medium prepared by supplementing the basal medium with BMP4, retinoic acid, and a GSK3β inhibitor.

The term "BMP4" used herein refers to a protein encoded by the polynucleotide shown in the NCBI Accession Number NM_001202, NM_130850, or NM_130851, and it may be in an active form resulting from cleavage by a protease.

The BMP4 concentration in a culture solution is not particularly limited. For example, such concentration is 10 ng/ml to 1 μg/ml, and it is specifically 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml, 600 ng/ml, 700 ng/ml, 800 ng/ml, 900 ng/ml, or 1 μg/ml. The concentration is preferably 20 ng/ml.

While all-trans retinoic acid (ATRA) is exemplified as retinoic acid, artificially modified retinoic acid that retains functions of naturally occurring retinoic acid may be used. Examples thereof include 4-[[(5,6,7,8-tetrahydro-5,5,8,8-tetramethyl-2-naphthalenyl)carbonyl]amino]-benzoic acid (AM580) (Tamura, K. et al., Cell Differ. Dev., 32: 17-26, 1990), 4-[(1E)-2-(5,6,7,8-tetrahydro-5,5,8,8-tetramethyl-2-naphthalenyl)- 1-propen- 1-yl]-benzoic acid (TTNPB) (Strickland, S. et al., Cancer Res., 43: 5268-5272, 1983), retinol palmitate, retinol, retinal, 3-dehydroretinoic acid, 3-dehydroretinol, 3-dehydroretinal, and compounds described in Abe, E. et al., Proc. Natl. Acad. Sci., U.S.A., 78: 4990-4994, 1981; Schwartz, E. L. et al., Proc. Am. Assoc. Cancer Res., 24: 18, 1983; and Tanenaga, K. et al., Cancer Res., 40: 914-919, 1980.

The retinoic acid concentration in a medium is not particularly limited. For example, such concentration is 1 nM to 1 μM, and it is specifically 1 nM, 5 nM, 10 nM, 15 nM, 20 nM, 25 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, or 1 μM. The concentration is preferably 50 nM to 1 μM.

The GSK3β inhibitor as described above can be used in this step, and the GSK3β inhibitor is preferably CHIR99021. In this step, the CHIR99021 concentration in a medium is, for example, 1 nM to 50 μM, and it is specifically 1 nM, 10 nM, 50 nM, 100 nM, 500 nM, 750 nM, 1μM, 1.5 μM, 2 μM, 2.5 μM, 3 μM, 3.5 μM, 4 μM, 4.5 μM, 5 μM, 6 μM, 7 μM, 8 μM, 9 μM, 10 μM, 15 μM, 20 μM, 25 μM, 30 μM, 40 μM, or 50 μM, although the concentration is not limited thereto. In this step, the concentration is preferably 1.5 04 to 3.5 μM.

In this step, culture may be conducted in a culture vessel treated with a coating agent. A coating agent may be a naturally occurring or artificially synthesized extracellular matrix. Examples thereof include BD Matrigel, collagen, gelatin, laminin, heparan sulfate proteoglycan, entactin, and a combination of any thereof, with Matrigel being preferable.

This step may be implemented by exchanging the cell culture medium obtained in the previous step (a culture solution) with the medium described above (a culture solution). Alternatively, cells may be detached and reseeded in a culture vessel. When cells are to be detached, particular cells may be selected, and, for example, SOX2-, SOX17-, and/or FOXA2-positive cells may be selected and used in this step. This method is preferably implemented by means of media exchange.

When the step comprises a process of cell detachment, a ROCK inhibitor may be added to a medium, so as to inhibit pluripotent stem cell death caused by detachment.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period is at least 1 day, 2 days, 3 days, 4 days, 5 days, 6 days, 7 days, or 8 days. The culture period is preferably at least 4 days, and more preferably 4 days.

[Step of Isolating (Selecting) Ventral Anterior Foregut Cells]

The method of the present invention can further comprise, following Step (3), a step of isolating carboxypeptidase M (CPM)-positive cells as ventral anterior foregut cells. The isolated ventral anterior foregut cells can be used in Step (4) or (5). The isolated ventral anterior foregut cells may constitute a cell population including ventral anterior foregut cells. Preferably, the ventral anterior foregut cells account for 50%, 60%, 70%, 80%, or 90% or more of the cell population including ventral anterior foregut cells.

Ventral anterior foregut cells can be isolated with the use of reagents having specific affinity to CPM. Examples of reagents having specific affinity that can be used in the present invention include antibodies, aptamers, peptides, and compounds that specifically recognize the substances of interest, with antibodies or fragments thereof being preferable.

Antibodies may be polyclonal or monoclonal antibodies. Examples of antibody fragments include a part of an antibody (e.g., an Fab fragment) and a synthetic antibody fragment (e.g., a single-stranded Fv fragment, ScFv).

In order to recognize or separate cells that express CPM, reagents having relevant affinity may be bound or conjugated to substances that enable detection, such as a fluorescent label, a radioactive label, a chemoluminescent label, an enzyme, biotin, or streptoavidin, or substances that enable isolation and extraction, such as Protein A, Protein G, beads, or magnetic beads.

Alternatively, reagents having relevant affinity may be indirectly labeled. For example, pre-labeled antibodies (secondary antibodies) that specifically bind to the antibodies described above may be used.

Ventral anterior foregut cells can be isolated (extracted) by, for example, a method comprising conjugating particles to a reagent having relevant affinity in order to precipitate the cells, a method involving the use of magnetic beads to select the cells with the aid of magnetism (e.g., MACS), a method involving the use of a cell sorter with the aid of a fluorescent label (e.g., FACS), or a method involving the use of a support upon which antibodies or the like are immobilized (e.g., a cell enrichment column).

(4) Step of Ventral Anterior Foregut Cell culture in a Medium Containing a GSK3β Inhibitor and FGF10 (Step 4)

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, Glutamax (Invitrogen), nonessential amino acids, vitamins, growth factors, low-molecular-weight compounds, antibiotics, antioxidants, pyruvic acids, buffer agents, and inorganic salts. A medium mixture of DMEM and Ham's F12 supplemented with Glutamax, B27 supplement, L-ascorbic acid, monothioglycerol, penicillin, and streptomycin is preferable.

In this step, the ventral anterior foregut cells obtained in the previous step (i.e., the step of culture in a medium containing BMP4, retinoic acid, and a GSK3β inhibitor) are cultured in a medium prepared by supplementing the basal medium with a GSK3β inhibitor and FGF10.

The GSK3β inhibitor as described above can be used in this step, and the GSK3β inhibitor is preferably CHIR99021. In this step, the CHIR99021 concentration in a medium is, for example, 1 nM to 50 μM, and it is specifically 1 nM, 10 nM, 50 nM, 100 nM, 500 nM, 750 nM, 1 μM, 1.5 μM, 2 μM, 2.5 μM, 3 μM, 3.5 μM, 4 μM, 4.5 μM, 5 μM, 6 μM, 7 μM, 8 μM, 9 μM, 10 μM, 15 μM, 20 μM, 25 μM, 30 μM, 40 μM, or 50 μM, although the concentration is not limited thereto. In this step, the concentration is preferably 3 μM.

The term "FGF10" used herein refers to a protein encoded by the polynucleotide shown in the NCBI Accession Number NM_004465, and it may be in an active form resulting from cleavage by a protease. Such FGF10 is commercially available from, for example, Life Technologies or Wako.

The FGF10 concentration in a medium is not particularly limited. For example, such concentration is 1 ng/ml to 1 μg/ml, and it is specifically 1 ng/ml, 5 ng/ml, 10 ng/ml, 20 ng/ml, 50 ng/ml, 100 ng/ml, 200 ng/ml, 300 ng/ml, 400 ng/ml, 500 ng/ml, or 1 μg/ml. The concentration is preferably 100 ng/ml.

In this step, a ROCK inhibitor, such as Y-27632, may further be added to a medium. The Y-27632 concentration in a medium is, for example, 100 nM to 50 μM, and it is specifically 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, or 50 μM, although the concentration is not limited thereto. The concentration is preferably 10 μM.

In this step, culture may be conducted in a culture vessel treated with a coating agent. A coating agent may be a naturally occurring or artificially synthesized extracellular matrix. Examples thereof include Geltrex containing laminin, collagen IV, entactin, and heparin sulfate proteoglycan (Life Technologies), BD Matrigel, collagen, gelatin, laminin, heparan sulfate proteoglycan, entactin, and a combination of any thereof, with Geltrex being preferable.

This step may be implemented by exchanging the cell culture medium obtained in the previous step (a culture solution) with the medium described above (a culture solution). Alternatively, cells may be detached and reseeded in a culture vessel.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period is at least 2 days, 3 days, 4 days, 5 days, 6 days, 7 days, 8 days, 9 days, 10 days, 11 days, 12 days, 13 days, or 14 days. The culture period is preferably at least 14 days, and it is more preferably 14 days. When a ROCK inhibitor is to be added, such addition is carried out for 1 or 2 days, and preferably 2 days, after the initiation of this step.

(5) Step of Three-dimensional Culture of Ventral Anterior Foregut Cells or Airway Epithelial Progenitor Cells in a Medium Containing a GSK3β Inhibitor, FGF10, and a ROCK Inhibitor (Step 5)

When Step (4) (i.e., a step of ventral anterior foregut cell culture in a medium containing a GSK3β inhibitor and FGF10) is not carried out, the ventral anterior foregut cells obtained in Step (3) is subjected to this step. When Step (4) is carried out, in contrast, the airway epithelial progenitor cells obtained in Step (4) is subjected to this step.

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, ITS Premix, collagen precursors, trace elements, 2-mercaptoethanol, and 3'-thiol glycerol. In addition, a medium can contain one or more substances selected from among, for example, lipids, amino acids, L-glutamine, Glutamax (Invitrogen), nonessential amino acids, vitamins, growth factors, low-molecular-weight compounds, antibiotics, antioxidants, pyruvic acids, buffer agents, and inorganic salts. A medium mixture of DMEM and Ham's F12 supplemented with Glutamax, B27 supplement, L-ascorbic acid, monothioglycerol, penicillin, and streptomycin is preferable.

In this step, ventral anterior foregut cells or alveolar epithelial progenitor cells are cultured in a medium prepared by supplementing the basal medium with a GSK3β inhibitor, FGF10, and a ROCK inhibitor.

The GSK3β inhibitor as described above can be used in this step, and the GSK3β inhibitor is preferably CHIR99021. In this step, the CHIR99021 concentration in a medium is, for example, 1 nM to 50 μM, and it is specifically 1 nM, 10 nM, 50 nM, 100 nM, 500 nM, 750 nM, 1 μM, 1.5 μM, 2 μM, 2.5 μM, 3 μM, 3.5 μM, 4 μM, 4.5 μM, 5 μM, 6 μM, 7 μM, 8 μM, 9 μM, 10 μM, 15 μM, 20 μM, 25 μM, 30 μM, 40 μM, or 50 μM, although the concentration is not limited thereto. In this step, the concentration is preferably 3 μM.

In this step, the FGF10 concentration in a medium is not particularly limited. For example, such concentration is 1 ng/ml to 1 μg/ml, and it is specifically 1 ng/ml, 5 ng/ml, 10 ng/ml, 20 ng/ml, 50 ng/ml, 100 ng/ml, 200 ng/ml, 300 ng/ml, 400 ng/ml, 500 ng/ml, or 1 μg/ml. The concentration is preferably 100 ng/ml.

The ROCK inhibitor as described above can be used in this step, and the ROCK inhibitor is preferably Y-27632. The Y-27632 concentration in a medium is, for example, 100 nM to 50 μM, and it is specifically 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, or 50 μM, although the concentration is not limited thereto. The concentration is preferably 10 μM.

This step may be implemented by detaching the cells obtained in the previous step and reseeding the cells in a culture vessel. When cells are to be detached, particular cells may be selected, and, for example, FOXJ1-, CFTR-, P63-, MUCSAC-, and/or NKX2-1-positive cells may be selected as airway epithelial progenitor cells obtained in Step (4) and used in this step.

In this step, ventral anterior foregut cells or airway epithelial progenitor cells are subjected to three-dimensional culture for maturation. The term "three-dimensional culture" used herein refers to float culture of cells in the form of cell masses (i.e., spheroids). Three-dimensional culture can be carried out with the use of, for example, Cell Culture Inserts provided by BD.

Three-dimensional culture is preferably conducted without the need of coculture; however, it may be conducted in the presence of other cell species. Examples of other cell species that may be used include human pulmonary fibroblasts and human fetal pulmonary fibroblasts. Such cells are commercially available from, for example, American Type Culture Collection (ATCC) and DV Biologics. Ventral anterior foregut cells or airway epithelial progenitor cells may be mixed with other cell species at a ratio of, for example, 1:10 to 500.

A cell density in the medium is, for example, $0.5\times10^6$ cells to $2\times10^7$ cells/ml, and preferably $4.0\times10^6$ cells /ml.

The medium used for three-dimensional culture may be prepared with the addition of an extracellular matrix to the medium described above. The ratio of the volume of the medium to the volume of the extracellular matrix is, for example, 1:0.25 to 10, and preferably 1:1. An extracellular matrix is a supramolecular structure that exists outside the cell, and it may be a naturally occurring or artificial (recombinant or peptide hydrogel) structure. Examples thereof include substances, such as collagen, proteoglycan, fibronectin, hyaluronic acid, tenascin, entactin, elastin, fibrillin, and laminin, and fragments thereof. These extracellular matrices may be used in combination. For example, extracellular matrices may be prepared from cells such as Corning Matrigel™. An example of an artificial structure is a laminin fragment or Corning PuraMatrix™.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period is at least 5 days, 6 days, 7 days, 8 days, 9 days, 10 days, 11 days, 12 days, 13 days, 14 days, 16 days, 18 days, 21 days, 24 days, 26 days, 28 days, 30 days, 32 days, 35 days, or 42 days. When Step (4) is not carried out, the culture period is preferably at least 28 days, and particularly preferably 28 days. When Step (4) is carried out, the culture period is preferably at least 14 days, and particularly preferably 14 days.

(6) Step of Subjecting Proximal Airway Epithelial Progenitor Cells to Three-dimensional Culture in a Medium Containing a ROCK Inhibitor (Step 6)

A medium used in this step can be prepared from a medium used for animal cell culture as a basal medium. Examples of basal media include Pneumacult-ALI Maintenance Medium (i.e., a medium prepared by supplementing Pneumacult-ALI Complete Base Medium, which contains Pneumacult-ALI Basal Medium and Pneumacult-ALI 10x Supplement, with Pneumacult-ALI Maintenance Supplement, hydrocortisone, and heparin) (STEMCELL Technologies), IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, ITS Premix, collagen precursors, trace elements, 2-mercaptoethanol, and 3'-thiol glycerol. In addition, a medium can contain one or more substances selected from among, for example, lipids, amino acids, L-glutamine, Glutamax (Invitrogen), nonessential amino acids, vitamins, growth factors, low-molecular-weight compounds, antibiotics, antioxidants, pyruvic acids, buffer agents, and inorganic salts. Pneumacult-ALI Maintenance Medium is preferable.

This step is implemented via culture of the proximal airway epithelial progenitor cells obtained by the previous step (i.e., the step of three-dimensional culture of ventral anterior foregut cells or airway epithelial progenitor cells in a medium containing a GSK3β inhibitor, FGF10, and a ROCK inhibitor) in a medium prepared by supplementing the basal medium described above with a ROCK inhibitor.

The ROCK inhibitor as described above can be used in this step, and the ROCK inhibitor is preferably Y-27632. The Y-27632 concentration in a medium is, for example, 100 nM to 50 μM, and it is specifically 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, or 50 μM, although the concentration is not limited thereto. The concentration is preferably 10 μM.

In this step, a NOTCH signal inhibitor is further added to a medium, so that differentiation into ciliated airway epithelial cells among airway epithelial cells can be accelerated.

The term "NOTCH signal inhibitor" used herein refers to a substance that inhibits a Notch signal. Examples thereof include DAPT (N-[2S-(3,5 -difluorophenyl)acetyl]-L-alanyl-2-phenyl-1,1-dimethylethyl ester-glycine), DBZ (N-[(1S)-2-[[(7S)-6,7-dihydro-5-methyl-6-oxo-5H-dibenz[b,d] azepin-7-yl]amino]-1-methyl-2-oxoethyl]-3,5 -difluorobenzeneacetamide), Compound E (N-[(1S)-2-[[(3S)-2,3-dihydro-1-methyl-2-oxo-5-phenyl-1H-1,4-benzodiazepin-3-yl]-amino]-1-methyl-2-oxoethyl]-3,5-difluorobenzeneacetamide), FLI-06 (cyclohexyl 1,4,5,6,7,8-hexahydro-2,7 ,7-trimethyl-4-(4-nitrophenyl)-5-oxo-3 -quinolinecarboxylate), and LY411575 (N2-[(2S)-2-(3,5-difluorophenyl)-2-hydroxyethanoyl]-N1-[(7S)-5-methyl-6-oxo-6,7-dihydro-5H-dibenzo[b,d] azepin-7-yl]-L-alaninamide).

A NOTCH signal inhibitor that can be preferably used in this step is DAPT. The DAPT concentration in a medium is not particularly limited, provided that a Notch signal is inhibited. For example, such concentration is 1 nM to 50 μM, and it is specifically 1 nM, 10 nM, 50 nM, 100 nM, 500 nM, 750 nM, 1 μM, 1.5 μM, 2 μM, 2.5 μM, 3 μM, 3.5 μM, 4 μM, 4.5 μM, 5 μM, 6 μM, 7 μM, 8 μM, 9 μM, 10 μM, 15 μM, 20 μM, 25 μM, 30 μM, 40 μM, or 50 μM. The concentration is preferably 10 μM.

This step may be implemented by exchanging the cell culture medium obtained in the previous step (a culture solution) with the medium described above (a culture solution). Alternatively, cells may be detached and reseeded in a culture vessel. When cells are to be detached, particular cells may be selected, and, for example, SOX2-and NKX2-1-positive cells may be selected as the proximal airway epithelial progenitor cells obtained in Step (5) and used in this step.

In this step, proximal airway epithelial progenitor cells are subjected to three-dimensional culture for maturation. In this step, three-dimensional culture can be carried out in accordance with the process described with regard to Step (5) above.

The culture period is not particularly limited because long-term culture would not cause any problems. For example, the culture period is at least 5 days, 6 days, 7 days, 8 days, 9 days, 10 days, 11 days, 12 days, 13 days, or 14 days. The culture period is preferably at least 14 days, and it is more preferably 14 days.

[Step of Isolating (Selecting) Each Airway Epithelial Cell]

The method of the present invention can further comprise, following step (6), a step of isolating cells positive for one or more ciliated airway epithelial cell markers selected from the group consisting of Sentan (SNTN), FOXJ1 (Forkhead box J1), and DNAHS (dynein, axonemal, heavy chain 5) as ciliated airway epithelial cells.

Ciliated airway epithelial cells can be isolated in accordance with the above-described method for isolating CPM-positive cells as ventral anterior foregut cells. The isolated ciliated airway epithelial cells may constitute a cell population including ciliated airway epithelial cells. Preferably, the ciliated airway epithelial cells account for 5%, 10%, 20%, 30%, 40%, 50%, 60%, 70%, 80%, or 90% or more of the cell population including ciliated airway epithelial cells.

Similarly, airway mucin-producing cells can be isolated by selecting cells positive for one or more airway mucin-producing cell markers selected from the group consisting of MUCSAC (mucin SAC), AGR2 (anterior gradient 2), and SPDEF (SAM-pointed domain containing ets transcription factor), basal airway epithelial cells can be isolated by selecting cells positive for one or more basal airway epithelial cell markers selected from the group consisting of KRTS (keratin 5), NGFR (nerve growth factor receptor), and p63, and Club cells can be isolated by selecting cells positive for one or more Club cell markers: that is, SCGB1A1 (secretoglobin, family 1A, member 1) and/or SCGB3A2 (secretoglobin, family 3A, member 2).

[Pluripotent Stem Cells]

Pluripotent stem cells that can be used in the present invention are stem cells that have the potential to differentiate into any types of cells existing in organisms (i.e., pluripotency) and have the potential to grow. Examples thereof include embryonic stem cells (ES cells), nuclear transfer-derived embryonic stem cells from cloned embryos (nt ES cells), sperm stem cells (GS cells), embryonic germ cells (EG cells), induced pluripotent stem cells (iPS cells), and pluripotent cells derived from cultured fibroblasts and myeloid stem cells (Muse cells). In the present invention, the use of iPS cells or Muse cells is preferable because cells of interest can be obtained without destroying embryos.

(A) Embryonic Stem Cells

ES cells are pluripotent stem cells having the potential to grow through autoreproduction, and they are established from embryoblasts of early embryos (e.g., blastocysts) of mammalians such as humans or mice.

ES cells are embryo-derived stem cells originating from embryoblasts of blastocysts, which are embryos after the 8-cell stage and the morula stage of fertilized eggs. Such ES cells have the potential to differentiate into any types of cells constituting an adult; that is, so-called pluripotency, and the potential to grow through autoreproduction. ES cells were discovered in mice in 1981 (M. J. Evans and M. H. Kaufman, 1981, Nature 292: 154-156). Thereafter, ES cells of primates, such as humans and monkeys, were also established (J. A. Thomson et al., 1998, Science 282: 1145-1147; J. A. Thomson et al., 1995, Proc. Natl. Acad. Sci., U.S.A., 92: 7844-7848; J. A. Thomson et al., 1996, Biol. Reprod., 55: 254-259; J. A. Thomson and V. S. Marshall, 1998, Curr. Top. Dev. Biol., 38: 133-165).

ES cells can be established by extracting embryoblasts from blastocysts of fertilized eggs of target animals and culturing the embryoblasts on fibroblast feeders. Cells can be maintained via subculture with the use of a culture solution supplemented with substances such as leukemia inhibitory factors (LIF) and basic fibroblast growth factors (bFGF). Human and monkey ES cells can be established and maintained by the methods described in, for example, U.S. Pat. No. 5,843,780; Thomson J. A. et al., 1995, Proc. Natl. Acad. Sci., U.S.A., 92: 7844-7848; Thomson, J. A. et al., 1998, Science 282: 1145-1147; H. Suemori et al., 2006, Biochem. Biophys. Res. Commun., 345: 926-932; M. Ueno et al., 2006, Proc. Natl. Acad. Sci. U.S.A., 103: 9554-9559; H. Suemori et al., 2001, Dev. Dyn., 222: 273-279; H. Kawasaki et al., 2002, Proc. Natl. Acad. Sci. U.S.A., 99: 1580-1585; and Klimanskaya I et al., 2006, Nature 444: 481-485.

Human ES cells can be maintained with the use of a medium for ES cell production, such as a DMEM/F-12 medium supplemented with 0.1 mM 2-mercaptoethanol, 0.1 mM nonessential amino acids, 2 mM L-glutamic acid, 20% KSR, and 4 ng/ml bFGF, at 37° C. in the presence of 5% $CO_2$ in a moist atmosphere (H. Suemori et al., 2006, Biochem. Biophys. Res. Commun., 345: 926-932). It is necessary that ES cells be subjected to subculture every 3 or 4 days. Subculture can be carried out with the use of, for example, 0.25% trypsin and 0.1 mg/ml collagenase IV in PBS containing 1 mM $CaCl_2$ and 20% KSR.

In general, ES cells can be selected via real-time PCR using the expression of a gene marker such as alkaline phosphatase, Oct-3/4, or Nanog as an indicator. When human ES cells are to be selected, in particular, the expression of a gene marker such as OCT-3/4, NANOG, or ECAD can be employed as an indicator (E. Kroon et al., 2008, Nat. Biotechnol., 26: 443-452).

Human ES cells (e.g., WA01 (H1) and WA09 (H9)) are available from the WiCell Research Institute, and KhES-1, KhES-2, and KhES-3 are available from the Institute for Frontier Medical Sciences, Kyoto University (Kyoto, Japan).

(B) Sperm Stem Cells

Sperm stem cells are testis-derived pluripotent stem cells that serve as sources for spermatogenesis. As with the case of ES cells, sperm stem cells can be differentiated into various types of cells. For example, sperm stem cells may be implanted into mouse blastocysts, so that chimeric mice may be produced (M. Kanatsu-Shinohara et al., 2003, Biol. Reprod., 69: 12-616; K. Shinohara et al., 2004, Cell, 119: 1001-1012). Sperm stem cells are capable of autoreproduction in a medium containing glial cell line-derived neurotrophic factors (GDNF). In addition, sperm stem cells can be obtained by repeating subculture under the same culture conditions as with those used for ES cells (Masanori Takebayashi et al., 2008, Experimental Medicine, Vol. 26, No. 5 (extra edition), pp. 41-46, Yodosha, Tokyo, Japan).

(C) Embryonic Germ Cells

As with ES cells, embryonic germ cells are pluripotent cells that are established from primordial germ cells during the prenatal period. Embryonic germ cells can be established by culturing primordial germ cells in the presence of substances such as LIF, bFGF, or stem cell factors (Y. Matsui et al., 1992, Cell, 70: 841-847; J. L. Resnicket al., 1992, Nature, 359: 550-551).

(D) Induced Pluripotent Stem Cells

Induced pluripotent stem (iPS) cells can be prepared by introducing particular reprogramming factors into somatic cells in the form of DNA or proteins. iPS cells are artificial stem cells derived from somatic cells that have substantially the same properties as ES cells, such as pluripotency and the potential to grow through autoreproduction (K. Takahashi and S. Yamanaka, 2006, Cell, 126: 663-676; K. Takahashi et al., 2007, Cell, 131: 861-872; J. Yu et al., 2007, Science, 318: 1917-1920; Nakagawa, M. et al., Nat. Biotechnol., 26: 101-106, 2008; WO 2007/069666). Reprogramming factors may be composed of genes that are expressed specifically in ES cells, gene products or non-cording RNA thereof, genes that play key roles in maintenance of the undifferentiated state of ES cells, gene products or non-coding RNA thereof, or low-molecular-weight compounds. Examples of genes included in reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tc11, beta-catenin, Lin28b, Sal11, Sa114, Esrrb, Nr5a2, Tbx3, and Glis1. Such reprogramming factors may be used alone or in combination. Examples of combinations of reprogramming factors are described in WO 2007/069666, WO 2008/118820, WO 2009/007852, WO 2009/032194, WO 2009/058413, WO 2009/057831, WO 2009/075119, WO 2009/079007, WO 2009/091659, WO 2009/101084, WO 2009/101407, WO 2009/102983, WO 2009/114949, WO 2009/117439, WO 2009/126250, WO 2009/126251, WO 2009/126655, WO 2009/157593, WO 2010/009015, WO 2010/033906, WO 2010/033920, WO 2010/042800, WO 2010/050626, WO 2010/056831, WO 2010/068955, WO 2010/098419, WO 2010/102267, WO 2010/111409, WO 2010/111422, WO 2010/115050, WO 2010/124290, WO 2010/147395, WO 2010/147612, Huangfu, D. et al., 2008, Nat. Biotechnol., 26: 795-797, Shi, Y. et al., 2008, Cell Stem Cell, 2: 525-528, Eminli, S. et al., 2008, Stem Cells, 26: 2467-2474, Huangfu, D. et al., 2008, Nat. Biotechnol., 26: 1269-1275, Shi, Y. et al., 2008, Cell Stem Cell, 3, 568-574, Zhao, Y. et al., 2008, Cell Stem Cell, 3: 475-479, Marson, A. 2008, Cell Stem Cell, 3, 132-135, Feng, B. et al., 2009, Nat Cell Biol., 11: 197-203, R. L. Judson et al., 2009, Nat. Biotech., 27: 459-461, Lyssiotis, C.A. et al., 2009, Proc. Natl. Acad. Sci., U.S.A. 106: 8912-8917, Kim, J.B. et al., 2009, Nature, 461: 649-643, Ichida, J. K. et al., 2009, Cell Stem Cell, 5: 491-503, Heng, J.C. et al., 2010, Cell Stem Cell, 6: 167-74, Han, J. et al., 2010, Nature, 463: 1096-100, Mali, P. et al., 2010, and Stem Cells, 28: 713-720, Maekawa, M. et al., 2011, Nature, 474: 225-9.

Factors that are used to enhance cell establishment efficiency are within the scope of the reprogramming factors described above. Examples thereof include: histone deacetylase (HDAC) inhibitors, such as low-molecular-weight inhibitors, including valproic acid (VPA), trichostatin A, sodium butyrate, MC 1293, and M344, and nucleic acid-based expression inhibitors, including siRNAs and shRNAs against HDAC (e.g., HDAC1 siRNA Smartpool® (Millipore) and HuSH 29mer shRNA constructs against HDAC1 (OriGene)); MEK inhibitors (e.g., PD184352, PD98059, U0126, SL327, and PD0325901); glycogen synthase kinase-3 inhibitors (e.g., Bio and CHIR99021); DNA methyltransferase inhibitors (e.g., 5-azacytidine); histone methyltransferase inhibitors (e.g., low-molecular-weight inhibitors, such as BIX-01294, and nucleic acid-based expression inhibitors against Suv39h1, Suv39h2, SetDB1 and G9a, such as siRNAs and shRNAs); an L-channel calcium agonist (e.g., Bayk8644); butyric acid, TGFβ inhibitor, and ALKS inhibitor (e.g., LY364947, SB431542, 616453, and A-83-01); p53 inhibitors (e.g., siRNA and shRNA against p53); ARID3A inhibitors (e.g., siRNA and shRNA against ARID3A), miRNA, such as miR-291-3p, miR-294, miR-295, and mir-302, Wnt signaling (e.g., soluble Wnt3a), neuro-peptide Y, prostaglandins (e.g., prostaglandin E2 and prostaglandin J2), hTERT, SV4OLT, UTF1, IRX6, GLIS1, PITX2, and DMRTB1. Such factors used to enhance cell establishment efficiency are not particularly distinguished from reprogramming factors herein.

When reprogramming factors are in the form of proteins, for example, they may be introduced into somatic cells by a technique such as lipofection, fusion with cell-permeable peptides (e.g., HIV-derived TAT and polyarginine), or microinjection.

In contrast, reprogramming factors in the form of DNA can be introduced into somatic cells by a technique involving the use of a vector such as a virus, plasmid, or artificial chromosome vector, lipofection, a technique involving the use of a liposome, or microinjection, for example. Examples of virus vectors include retrovirus vectors, lentivirus vectors (Cell, 126, pp. 663-676, 2006; Cell, 131, pp. 861-872, 2007; Science, 318, pp. 1917-1920, 2007), adenovirus vectors (Science, 322, 945-949, 2008), adeno-associated virus vectors, and Sendai virus vectors (WO 2010/008054). Examples of artificial chromosome vectors include human artificial chromosome (HAC) vectors, yeast artificial chromosome (YAC) vectors, and bacterial artificial chromosome (BAC, PAC) vectors. Plasmids for mammalian animal cells can be used (Science, 322: 949-953, 2008). Vectors can comprise regulatory sequences, such as promoters, enhancers, ribosome-binding sequences, terminators, or polyadenylation sites, so that nuclear reprogramming substances can express. In addition, vectors can comprise selection marker sequences, such as drug tolerance genes (e.g., kanamycin tolerance genes, ampicillin tolerance genes, and puromycin tolerance genes), thymidine kinase genes, or diphtheria toxin genes, and reporter gene sequences, such as green fluorescent proteins (GFP), β-glucuronidase (GUS), or FLAG, according to need. The vector may comprise LoxP sequences in positions downstream and upstream of a gene encoding a reprogramming factor or a gene encoding a promoter and a reprogramming factor binding thereto, so as to eliminate such gene after the vector is introduced into somatic cells.

When reprogramming factors are in the form of RNA, for example, they may be introduced into somatic cells by a technique such as lipofection or microinjection. Alternatively, RNA comprising 5-methylcytidine and pseudouridine (TriLink Biotechnologies) incorporated therein may be used, so as to suppress degradation (Warren L, 2010, Cell Stem Cell 7: 618-630).

Examples of culture media used for iPS cell induction include DMEM containing 10% to 15% FBS, a DMEM/F12 or DME medium (such medium may adequately contain, for example, LIF, penicillin/streptomycin, puromycin, L-glutamine, nonessential amino acids, and β-mercaptoethanol), commercially available culture media (e.g., a medium for mouse ES cell culture; TX-WES medium, Thrombo X), a medium for primate ES cell culture (a medium for primate ES/iPS cell culture, ReproCELL Incorporated), and a serum-free medium (mTeSR, Stemcell Technology).

For example, somatic cells are brought into contact with reprogramming factors in a 10% FBS-containing DMEM or DMEM/F12 medium, culture is conducted at 37° C. in the presence of 5% $CO_2$ for about 4 to 7 days, and the cells are reseeded on feeder cells (e.g., mitomycin C-treated STO cells or SNL cells). Culture is reinitiated in a medium for bFGF-containing primate ES cell culture about 10 days after the somatic cells are first brought into contact with the reprogramming factors, and iPS-like colonies can then be formed at least about 30 to 45 days after such contact.

Alternatively, culture may be conducted in a 10% FBS-containing DMEM medium (this medium can further contain LIF, penicillin/streptomycin, puromycin, L-glutamine, nonessential amino acids, β-mercaptoethanol, or the like, according to need) on feeder cells (e.g., mitomycin C-treated STO cells or SNL cells) at 37° C. in the presence of 5% $CO_2$, and ES-like colonies can then be formed at least about 25 to 30 days later. Alternatively, use of the somatic cells to be reprogrammed instead of feeder cells is preferable (Takahashi K, et al., 2009, PLoS One, 4: e8067 or WO 2010/137746), or use of an extracellular matrix (e.g., laminin-5 (WO 2009/123349) and Matrigel (BD)) is preferable.

In addition, culture may be conducted with the use of a serum-free medium (Sun, N. et al., 2009, Proc. Natl. Acad. Sci., U.S.A. 106: 15720-15725). In order to enhance cell establishment efficiency, iPS cells may be established under low-oxygen conditions (oxygen concentration of 0.1% to 15%) (Yoshida, Y. et al., 2009, Cell Stem Cell, 5: 237-241 or WO 2010/013845).

During the culture, medium exchange is initiated 2 days after the initiation of culture, and the medium is exchanged with a fresh medium once a day. The number of somatic cells used for nuclear reprogramming is not limited, and it is about $5\times10^3$ to about $5\times10^6$ cells per 100 $cm^2$ of a culture dish.

iPS cells can be selected in accordance with the configuration of the formed colonies. When drug tolerance genes that express in association with genes that express upon reprogramming of somatic cells (e.g., Oct3/4 and Nanog) are introduced as marker genes, in contrast, culture can be conducted in a medium containing corresponding drugs (i.e., a selection medium). Thus, established iPS cells can be selected. When marker genes are fluorescent protein genes, fluorescent microscopic observation may be carried out. When marker genes are luminescent enzyme genes, luminescent substrates may be added. When marker genes are chromogenic enzyme genes, chromogenic substrates may be added. Thus, iPS cells can be selected.

The term “somatic cells” used herein refers to any animal cells except for germline cells or pluripotent cells such as egg cells, oocytes, and ES cells (preferably mammalian animal cells, including those of humans). Examples of somatic cells include, but are not limited to, embryonic (fetal) somatic cells, neonatal (fetal) somatic cells, and mature healthy or affected somatic cells. Somatic cells may be primary-cultured cells, subcultured cells, or established cells. Specific examples of somatic cells include: (1) tissue stem cells, such as neural stem cells, hematopoietic stem cells, mesenchymal stem cells, and dental pulp stem cells (i.e., somatic stem cells); (2) tissue progenitor cells; and (3) differentiated cells, such as lymphocytes, epidermic cells, endothelial cells, muscle cells, fibroblasts (e.g., skin cells), hair cells, hepatic cells, gastric mucosal cells, intestinal cells, splenic cells, pancreatic cells (e.g., pancreatic exocrine cells), brain cells, pneumocytes, nephrocytes, and adipocytes.

When iPS cells are used as materials for transplantation, use of somatic cells having the same or substantially the same HLA genotype as that of a recipient is preferable, so that rejection would not occur. When HLA genotypes are “substantially the same,” such HLA genotypes are concordant with each other to the extent that an immunosuppressive agent is able to suppress immune responses to the transplanted cells. For example, such somatic cells have HLA genotypes exhibiting concordance in 3 loci; i.e., HLA-A, HLA-B, and HLA-DR, or in 4 loci; i.e., HLA-A, HLA-B, HLA-DR, and HLA-C.

(E) Nuclear Transfer-derived ES Cells from Cloned Embryos

“nt ES cells” are nuclear transfer-derived ES cells produced from cloned embryos, and such ES cells have substantially the same properties as fertilized egg-derived ES cells (T. Wakayama et al., 2001, Science, 292: 740-743; S. Wakayama et al., 2005, Biol. Reprod., 72: 932-936; J. Byrne et al., 2007, Nature, 450: 497-502). Specifically, nuclear transfer ES cells (i.e., nt ES cells) are ES cells that are established from embryoblasts of blastocysts derived from cloned embryos resulting from substitution of an unfertilized egg nucleus with a somatic cell nucleus. nt ES cells are produced by the technique of nuclear transfer (J. B. Cibelli et al., Nature Biotechnol., 16: 642-646, 1998) in combination with the technique of ES cell production (Kiyoka Wakayama et al., Experimental Medicine, Vol. 25, No. 5 (extra edition), pp. 47-52, 2008). In the case of nuclear transfer, somatic cell nuclei are injected into enucleated unfertilized eggs of mammalian animals, and culture is conducted for several hours. Thus, such cells can be reprogrammed.

(F) Multilineage-differentiating Stress Enduring Cells (Muse Cells)

Muse cells are pluripotent stem cells produced by the method described in WO 2011/007900. More specifically, Muse cells are pluripotent cells that are obtained by treating fibroblasts or myeloid interstitial cells with trypsin for a long period of time (preferably for 8 hours or 16 hours) and conducting float culture. Such cells are positive for SSEA-3 and CD105.

[Kit for Producing Airway Epithelial Cells from Pluripotent Stem Cells]

The present invention provides a kit for producing airway epithelial cells from pluripotent stem cells. The kit may comprise growth factors, compounds, a medium, an extracellular matrix, a cell detachment solution, and an agent for coating the culture vessel used for induction of differentiation, as described above. The kit may further comprise documents and/or instructions describing the procedure for the induction of differentiation.

[Applications of Airway Epithelial Cells Obtained in the Present Invention]

Airway epithelial cells such as the ciliated airway epithelial cells obtained in the present invention can be used for elucidation of pathological conditions of diseases causing ciliary motility disorders or mucociliary clearance abnormalities, including congenital diseases, such as primary ciliary dyskinesia, cystic fibrosis, and A1-antitrypsin deficiency in the airways, and acquired diseases, such as bronchiectasia, asthma, and chronic obstructive pulmonary disease (COPD), and large-scale screening of candidate drugs in vitro when developing therapeutic agents for such diseases.

Airway epithelial cells such as the ciliated airway epithelial cells obtained in the present invention can be administered to patients afflicted with diseases causing ciliary motility disorders or mucociliary clearance abnormalities in the form of pharmaceutical preparations. The airway epithelial cells are prepared into the form of a sheet, and the sheet may be applied to the airway epithelium of a patient. Alternatively, the airway epithelial cells may be suspended in physiological saline or the like, and the suspension may then be directly implanted in the airways of the patient. Accordingly, the present invention provides an agent for treatment of airway diseases comprising airway epithelial cells obtained from pluripotent stem cells in the manner described above.

In the present invention, the number of airway epithelial cells contained in the agent for treatment of airway diseases is not particularly limited, provided that the transplanted grafts are able to survive after administration. The number of the cells may be adequately adjusted in accordance with lesion size or body size.

Hereafter, the present invention is described in greater detail with reference to the Examples, although the technical scope of the present invention is not limited to these Examples.

EXAMPLE 1

Method for Inducing Airway Epithelial Cells

1. Method for Inducing Airway Epithelial Cells

FIG. 1 shows a method for inducing airway epithelial cells from ventral anterior foregut cells using human pluripotent stem cells.

1-1. Induction of Differentiation from Human Pluripotent Stem Cells into Ventral Anterior Foregut Cells in Steps 1-3

In accordance with the method described in Gotoh, S. et al., Stem Cell Reports, Vol. 3, pp. 394-403, 2014, human pluripotent stem cells were induced to differentiate into ventral anterior foregut cells.

Human iPS cells (201B7, 585A1, 604A1) were provided by Professor Yamanaka at Kyoto University, human ES cells (H9) were provided by WiCell Research Institute, and the cells were cultured in accordance with a conventional technique (Takahashi, K. et al., Cell, 131: 861-872, 2007; Okita, K., et al., Stem Cells, 31: 458-466, 2013; Gotoh, S., et al., Stem Cell Reports, 3: 394-403, 2014).

The ventral anterior foregut cells were induced by detaching human pluripotent stem cells with the use of Accutase, seeding the cells in a 24-well plate coated with Matrigel at $2.0\times10^5$ cells/well or in a 6-well plate coated with Matrigel at $9.6\times10^5$ cells/well, and conducting culture under the conditions described below.

1-1-1. Step 1

The seeded cells (Day 0) were cultured in a basal medium (RPMI1640 (Nacalai Tesque) containing 2% B27 (Life Technologies) and a 0.5% penicillin/streptomycin stock solution (Life Technologies)) supplemented with 100 ng/ml activin A (R&D Systems), 1μM CHIR99021, and 10 μM Y-27632. On the following day (Day 1), the medium was exchanged with the above-described basal medium containing 100 ng/ml activin A, 1 μM CHIR99021, and 0.25 mM NaB, the medium was exchanged with another medium under the same conditions on the following day (Day 2) and 3 days later (Day 4), and culture was conducted for 5 days.

Alternatively, the seeded cells (Day 0) were cultured in the above-described basal medium supplemented with 100 ng/ml activin A, 1 μM CHIR99021, and 10 μM Y-27632. On the following day (Day 1), the medium was exchanged with the above-described basal medium containing 100 ng/ml activin A, 1 μM CHIR99021, 10 μM Y-27632, and 0.125 mM or 0.25 mM NaB. On the following day (Day 2), the medium was exchanged with the above-described basal medium containing 100 ng/ml activin A, 1 μM CHIR99021, and 0.125 mM or 0.25 mM NaB. The medium was then exchanged with another medium of the same conditions 3 days after the initiation of culture (Day 4).

1-1-2. Step 2

The cells obtained in Step 1 (Day 6) were cultured in a basal medium (DMEM/F12 medium (Life Technologies) containing 1% Glutamax supplement (Life Technologies), 2% B27 supplement, 1% N2 supplement (Life Technologies), 0.8% StemSure™ 50 mmol/1 monothioglycerol solution (Wako), 50 μg/ml L-ascorbic acid (Sigma Aldrich), and 0.5% penicillin/streptomycin stock solution) supplemented with 100 ng/ml hNoggin (R&D Systems) and 10 μM SB-431542 for 4 days. In this case, the medium was exchanged with another medium under the same conditions every other day.

1-1-3. Step 3

The cells obtained in Step 2 (Day 10) were cultured in the basal medium used in Step 2 containing 20 ng/ml hBMP4 (HumanZyme, Inc.), 0.05 μM, 0.5 μM, or 1.0 μM all-trans retinoic acid (ATRA), and 2.5 μM or 3.5 μM CHIR99021 for 4 days. In this case, the medium was exchanged with another medium under the same conditions every other day.

1-2. Two-dimensional culture in Step 4

The ventral anterior foregut cells on Day 14 (upon completion of Step 3) induced to differentiate in Section 1-1 above were cultured in the medium for Step 4 for 14 days and the airway epithelial progenitor cells were thus obtained efficiently.

On Day 14 after the induction of cell differentiation in Section 1-1 above (i.e., upon completion of Step 3), ventral anterior foregut cells were isolated via magnetic activated cell sorting (MACS) with the use of antibodies reacting with CPM. Y-27632 (10 μM) was added to the medium 1 hour before the ventral anterior foregut cells were peeled. Thereafter, the culture plate was washed with PBS (Nacalai Tesque), and 0.5 mM EDTA/PBS was added, followed by incubation at 37° C. for 12 minutes. After EDTA/PBS was removed, Accutase (Innovative Cell Technologies) was added, incubation was carried out at 37° C. for 25 minutes, a DMEM medium (Nacalai Tesque) supplemented with 2% FBS (Life Technologies) was added, and the cells were then recovered via pipetting. The recovered cell suspension was allowed to pass through a 40 μm cell strainer mesh (BD Falcon), and the resultant was centrifuged at 800 rpm for 5 minutes, followed by washing with 1% BSA/PBS. The mouse anti-human CPM antibody (Leica Microsystems) was added as the primary antibody, and the reaction was then allowed to proceed at 4° C. for 15 minutes.

After the completion of primary antibody treatment, the cells were washed two times with 2 mM EDTA/0.5% BSA/PBS, the magnetic microbead-labeled anti-mouse IgG1 antibody (Miltenyi Biotech) was added as the secondary antibody, and the reaction was allowed to proceed in the dark at 4° C. for 15 minutes. After the completion of secondary antibody treatment, the cells were washed two times with 2 mM EDTA/0.5% BSA/PBS, and propidium iodide was added in the end. Thereafter, CPM-positive cells were isolated via MACS with the use of magnetic metal columns (Miltenyi Biotec) and used as the ventral anterior foregut cells.

Separately, a 24-well plate was coated with 250 μl of 100-fold diluted Geltrex (Life Technologies) per well 2 hours before the ventral anterior foregut cells were seeded.

Subsequently, a suspension of $1.2 \times 10^6$ ventral anterior foregut cells isolated as CPM-positive cells in 500 μl of the medium for Step 4 was seeded, the medium for Step 4 was exchanged with another medium 2 days thereafter, and medium exchange was performed every other day. On the first 2 days, Y-27632 (LC Laboratories) was added to the final concentration of 10 μM.

The medium for Step 4 was prepared by supplementing a basal medium (DMEM/F12 medium (Life Technologies) containing 1× Glutamax supplement (Life Technologies), 1× B27 supplement (Life Technologies), 0.05 mg/ml L-ascorbic acid (Sigma Aldrich), 0.4 mM monothioglycerol (Wako), and 50 U/ml penicillin/streptomycin (Life Technologies)) with 3 μM CHIR99021 (Axon Medchem) and 100 ng/ml Fibroblast Growth Factor 10 (FGF10) (Wako).

1-3. Three-Dimensional Culture in Step 5

Y-27632 (10 μM) was added to the medium 1 hour before the airway epithelial progenitor cells were peeled on Day 28 (i.e., upon completion of Step 4). Thereafter, the culture plate was washed with PBS (Nacalai Tesque), and 0.5 mM EDTA/PBS was added thereto, followed by incubation at 37° C. for 5 minutes.

After EDTA/PBS was removed, Accutase (Innovative Cell Technologies) was added, incubation was carried out at 37° C. for 20 minutes, a DMEM medium (Nacalai Tesque) supplemented with 2% FBS (Life Technologies) was added, and the cells were then recovered via pipetting.

Following centrifugation at 800 rpm for 5 minutes, the supernatant was suctioned, and the remaining cell pellet was washed with 1% BSA/PBS. Airway epithelial progenitor cells ($4.5 \times 10^5$ cells) were suspended in 112 μl of the medium for Step 5, the resulting cell suspension was mixed with Matrigel (Corning) at a ratio of 1:1 by volume at a low temperature, the resulting mixture was immediately added to the upper layer, and 1 ml of the medium for Step 5 was added to the lower layer in each well of a 12-well plate Cell Culture Inserts (Corning). The medium for Step 5 in a lower layer was selectively exchanged with another medium 2 days thereafter, and such medium exchange was performed every other day.

The composition of the medium for Step 5 was different from that of the medium for Step 4 in terms of constant addition of 10 μM Y-27632.

1-4. Three-dimensional Culture in Step 6

On Day 42 (i.e., upon completion of Step 5), the medium in the lower layer of Cell Culture Inserts (Corning) was exchanged with the medium for Step 6, and the medium of the lower layer was selectively exchanged with another medium every other day.

The medium for Step 6 was prepared by supplementing the Pneumacult-ALI Maintenance Medium (STEMCELL Technologies) with 10 μM Y-27632. In addition, 10 μM DAPT (Wako) as a NOTCH signal inhibitor was added to the medium, and differentiation into ciliated airway epithelial cells was further accelerated.

The "Pneumacult-ALI Maintenance Medium" was prepared by supplementing the Pneumacult-ALI Complete Base Medium with 1 μM hydrocortisone (Sigma-Aldrich) and 4 μg/ml heparin (Nacalai Tesque) in accordance with the instructions provided by STEMCELL Technologies.

2. Results of Airway Epithelial Cell Induction

FIGS. 2 and 4 to 9 show the results of induction of differentiation from human iPS cells (201B7). It was confirmed that similar results can be attained from other human iPS cell lines (585A1, 604A1) and human ES cell lines (H9).

FIG. 2 shows double fluorescent immunostaining images of airway epithelial progenitor cells on Day 28 (i.e., upon completion of Step 4). Specifically, FIG. 2 shows that various marker proteins were expressed in NKX2.1-positive cells as airway/alveolar epithelial progenitor cell markers. FIGS. 2A to 2D show as follows.

FIG. 2A shows images demonstrating the results of staining of FOXJ1 and NKX2.1 as ciliated airway epithelial progenitor cell markers.

FIG. 2B shows images demonstrating the results of staining of CFTR and NKX2.1 as airway epithelial progenitor cell markers.

FIG. 2C shows images demonstrating the results of staining of P63 and NKX2.1 as basal airway epithelial progenitor cell markers.

FIG. 2D shows images demonstrating the results of staining of MUC5AC and NKX2.1 as airway mucin-producing progenitor cell markers.

As shown in FIG. 2, $NKX2.1^+FOXJ1^+$ cells (ciliated airway epithelial progenitor cells), $NKX2.1^+P63^+$ cells (basal airway epithelial progenitor cells), $NKX2.1^+MUC5AC^+$ cells (airway mucin-producing progenitor cells), and $NKX2.1^+CFTR^+$ cells (airway epithelial progenitor cells) were induced to differentiate by conducting Step 4.

Figure 3:
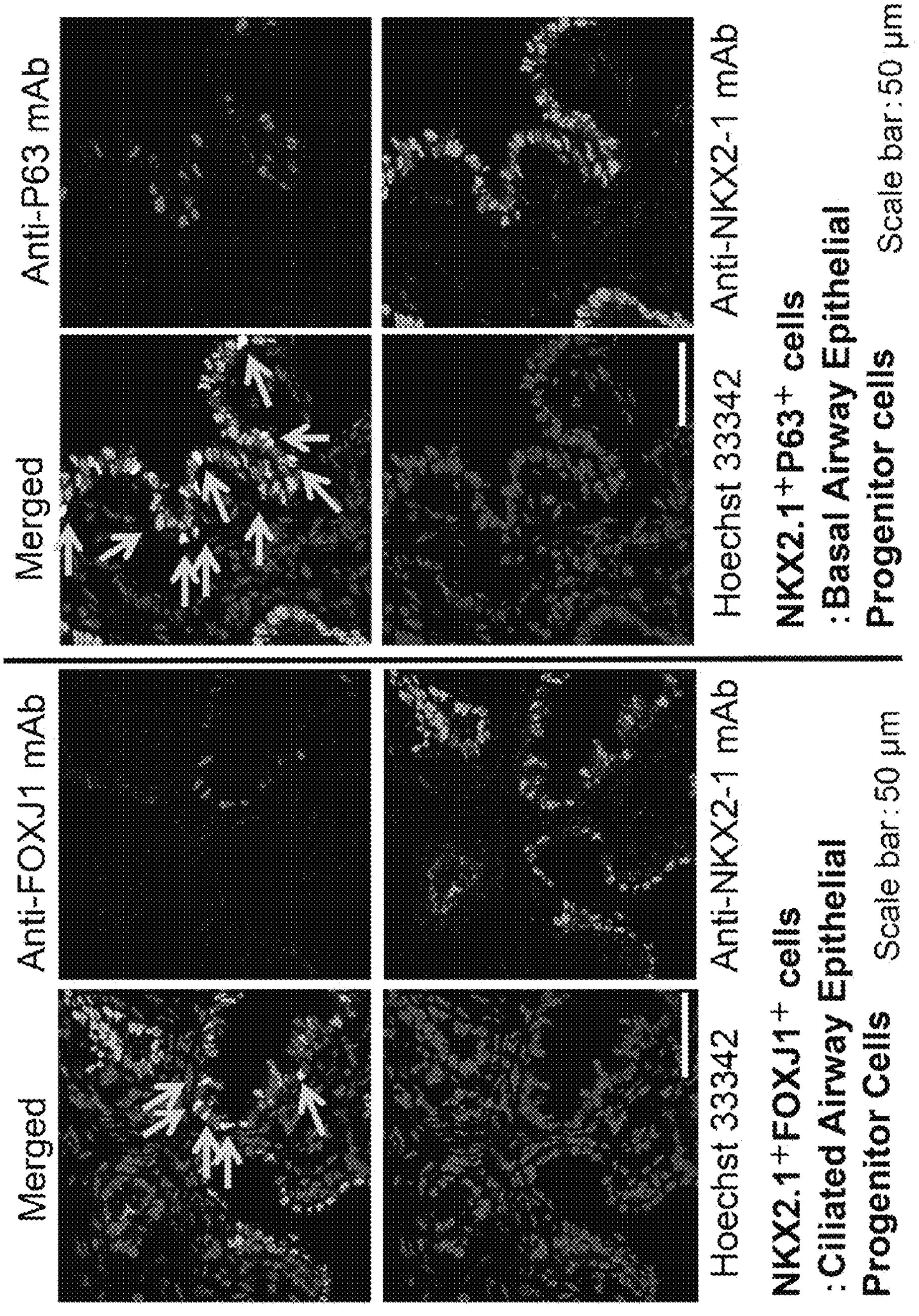
FIG. 3 shows fluorescent immunostaining images of $FOXJ1^{+}NKX2.1^{+}$ cells (indicated with arrows in images on the left) and $P63^{+}NKX2.1^{+}$ cells (indicated with arrows in images on the right) of human fetal pulmonary tissue (18.5-weeks pregnant).

FIG. 3 shows fluorescent immunostaining images of $FOXJ1^+NKX2.1^+$ cells (indicated with arrows in images on the left) and $P63^+NKX2.1^+$ cells (indicated with arrows in images on the right) of human fetal pulmonary tissue (18.5-weeks pregnant).

As shown in FIG. 3, NKX2.1 is not expressed in the airways of the adult lung, however, the presence of $NKX2.1^+FOXJ1^+$ cells and $NKX2.1^+P63^+$ cells was observed in the airways at the stage of the human fetal lung (18.5-weeks pregnant) (DV Biologics, PP001-FS, Lot.102508RH). That is, the method of induction of cell differentiation according to the present invention was in accordance with the developmental process.

Figure 4:
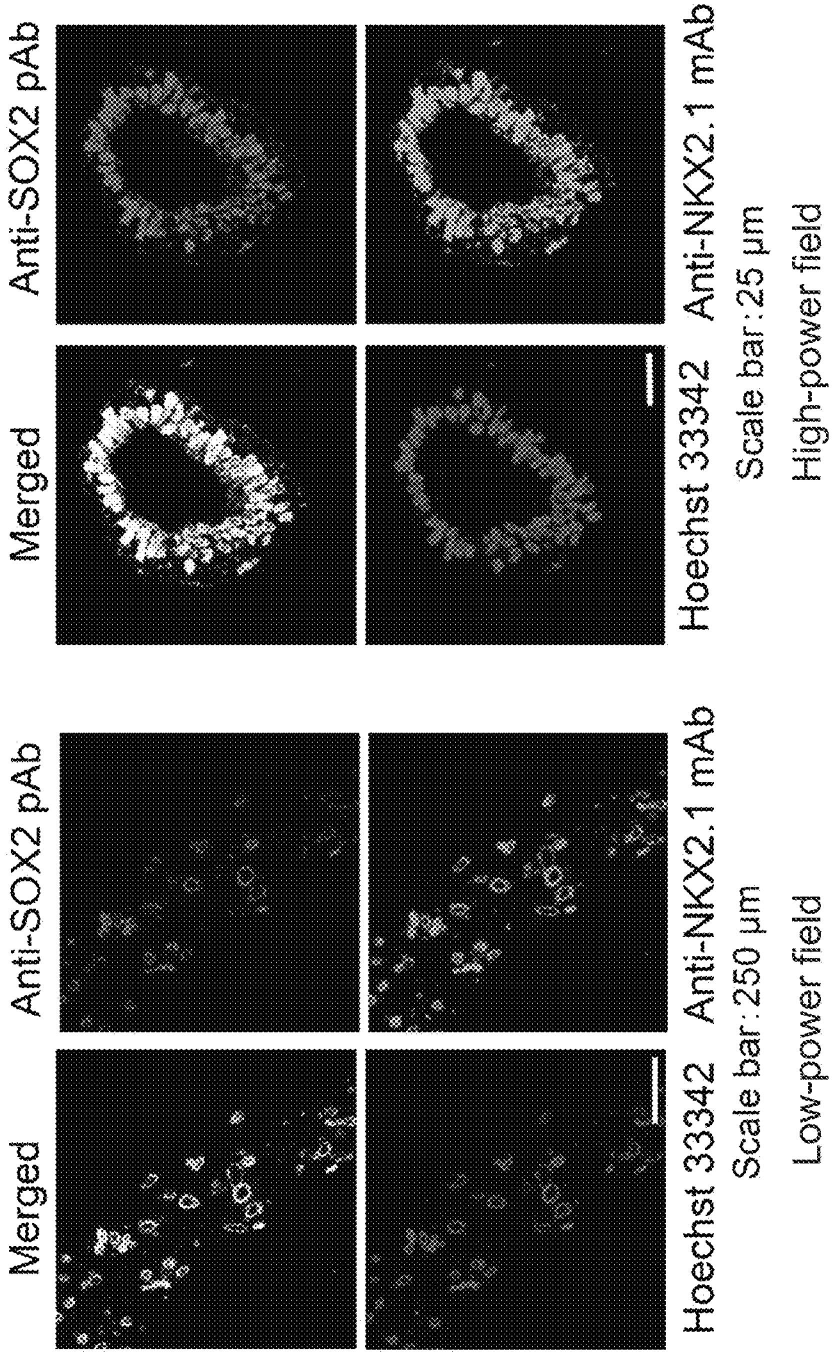
FIG. 4 shows fluorescent immunostaining images of spheroids formed from proximal airway epithelial progenitor cells on Day 42 (i.e., upon completion of Step 5) induced to differentiate with the use of human iPS cells (201B7).

FIG. 4 shows fluorescent immunostaining images of spheroids formed from proximal airway epithelial progenitor cells on Day 42 (i.e., upon completion of Step 5): i.e., co-stained images of SOX2 and NKX2.1 as proximal airway epithelial progenitor cell markers in low-power fields (images on the left); and those in high-power fields (images on the right).

As shown in FIG. 4, many spheroids were formed by conducting Step 5, substantially all the cells were $SOX2^+$ $NKX2.1^+$ cells representing the proximal airway epithelial progenitor cells, and these cells were not the distal airway epithelial progenitor cells.

Figure 5:
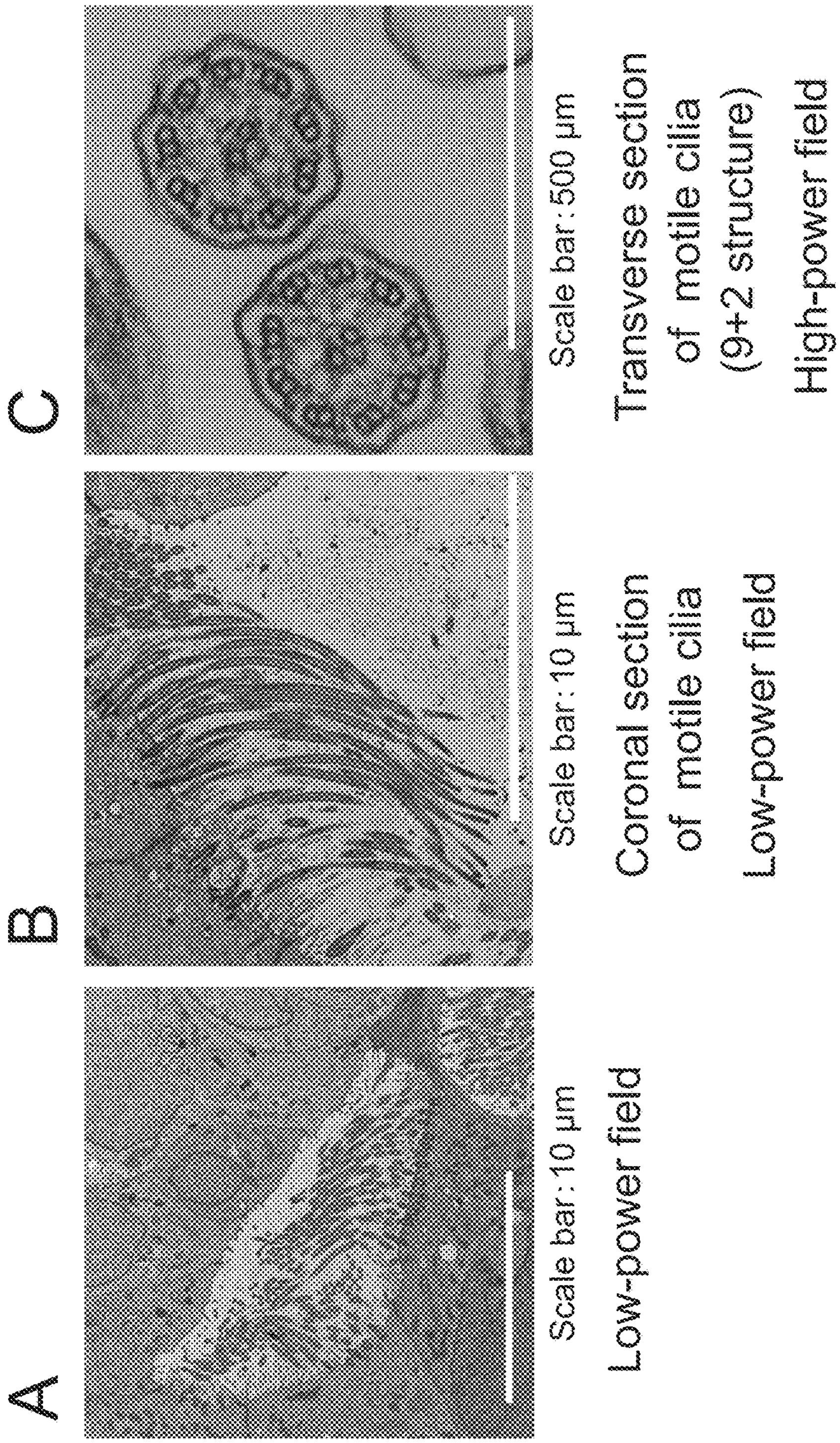
FIG. 5 shows transmission electron microscopic images on Day 56 (i.e., upon completion of Step 6) induced to differentiate with the use of human iPS cells (201B7).

FIG. 5 shows transmission electron microscopic images on Day 56 (i.e., upon completion of Step 5 for 14 days and Step 6 for 28 days without Step 4). FIGS. 5A to 5C show as follows.

FIG. 5A shows an image of one spheroid in a low-power field.

FIG. 5B shows a coronal section of cilia of ciliated airway epithelial cells.

FIG. 5C shows a 9+2 arrangement characteristics of dynamic cilia observed in the transverse section of the cilia.

Figure 6:
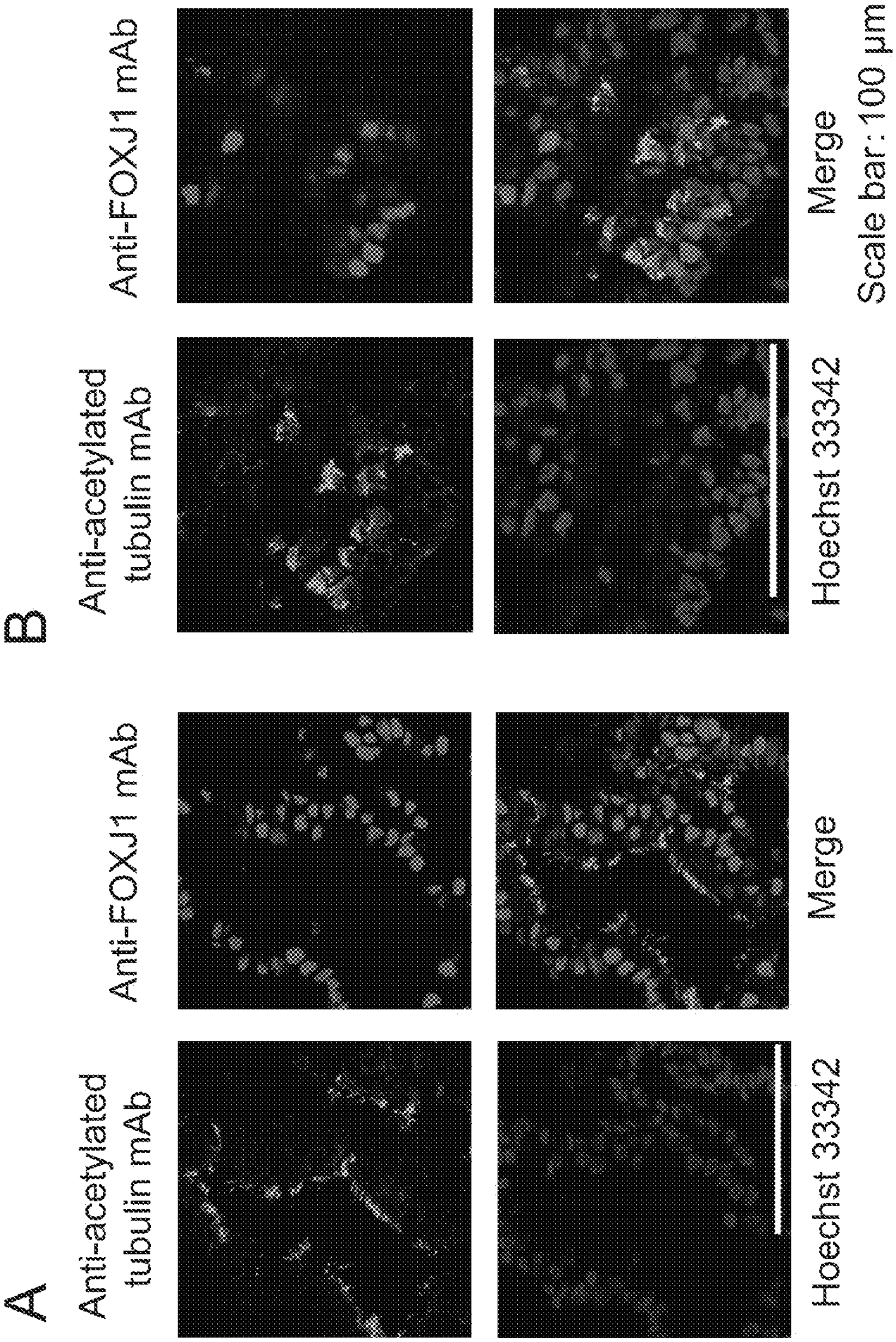
FIG. 6A shows fluorescent immunostaining images of spheroids including ciliated airway epithelial cells induced to differentiate with the use of human iPS cells (201B7) on Day 42 (i.e., upon completion of Step 5 for 14 days and Step 6 for 14 days without Step 4)
FIG. 6B shows those on Day 56 (i.e., upon completion of Step 4 for 14 days, Step 5 for 14 days, and Step 6 for 14 days).

FIG. 6A shows fluorescent immunostaining images of spheroids including ciliated airway epithelial cells induced to differentiate on Day 42 (i.e., upon completion of Step 5 for 14 days and Step 6 for 14 days without Step 4) and FIG. 6B shows those on Day 56 (i.e., upon completion of Step 4 for 14 days, Step 5 for 14 days, and Step 6 for 14 days). FIG. 6 shows images showing long cilia stained with acetylated tubulin growing in $FOXJ1^+$ cells as ciliated airway epithelial cells.

Figure 7:
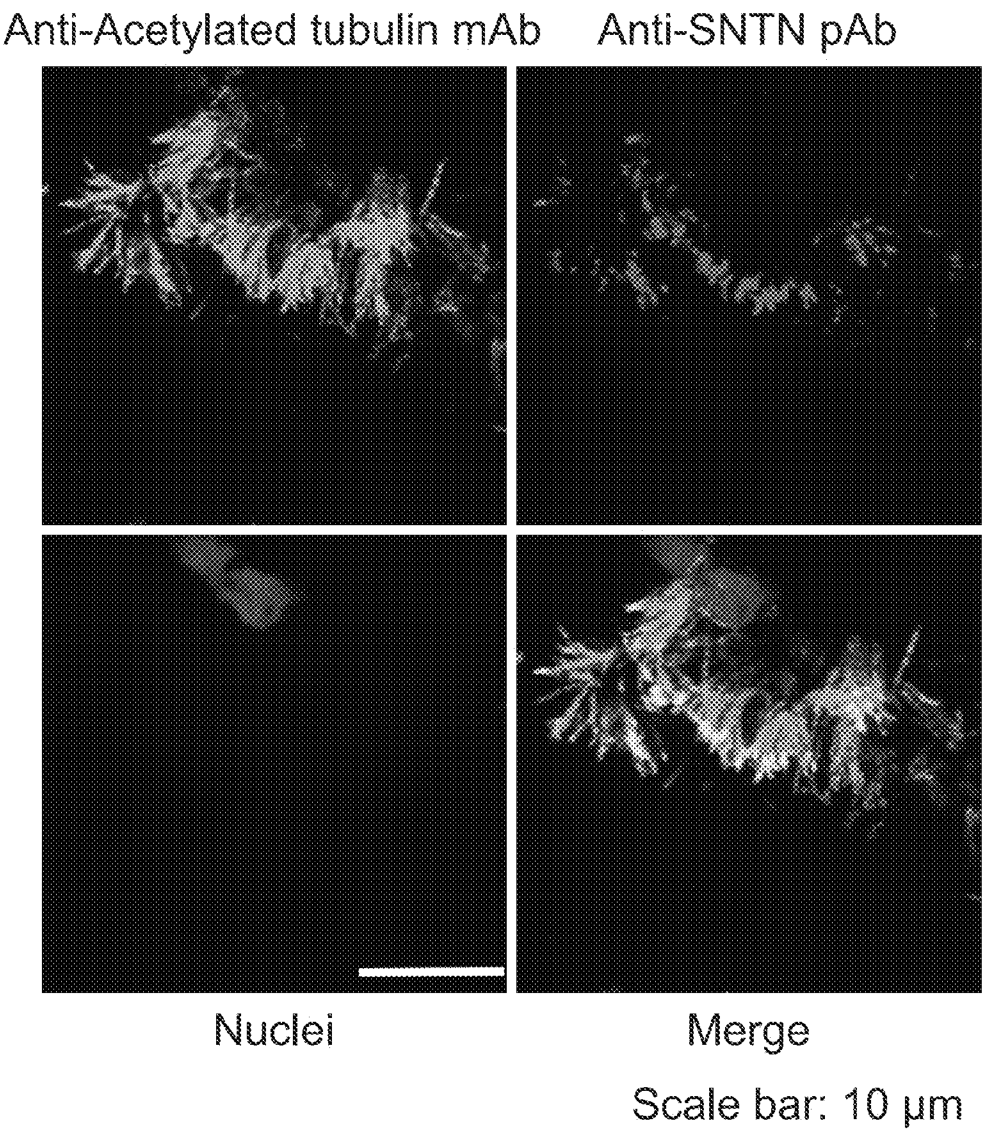
FIG. 7 shows fluorescent immunostaining images of ciliated airway epithelial cells induced to differentiate with the use of human iPS cells (201B7) on Day 56 (i.e., upon completion of Step 6).

FIG. 7 shows fluorescent immunostaining images of ciliated airway epithelial cells on Day 56 (i.e., upon completion of Step 6). FIG. 7 shows that Sentan (SNTN) as a marker protein specific for dynamic cilia was expressed at the end of long cilia stained with acetylated tubulin.

As shown in FIGS. 6 and 7, in addition to $NKX2.1^+$ $FOXJ1^+$ cells, ciliated airway epithelial cells ($SNTN^+$ $AcetylTub^+FOXJ1^+NKX2.1^+$ cells) expressing Sentan (SNTN) known as a protein marker specific for dynamic cilia were observed at the ends of many cilia positive for acetylated tubulin (AcetylTub) in epithelial cells constituting spheroids by conducting Step 6. Motions of cilia were observed in a culture dish. As shown in FIG. 5, also, a 9+2 arrangement characteristic as a cross section image of dynamic cilia was observed under the transmission electron microscope.

As described above, it was verified that differentiation into ciliated airway epithelial cells was induced.

Figure 8:
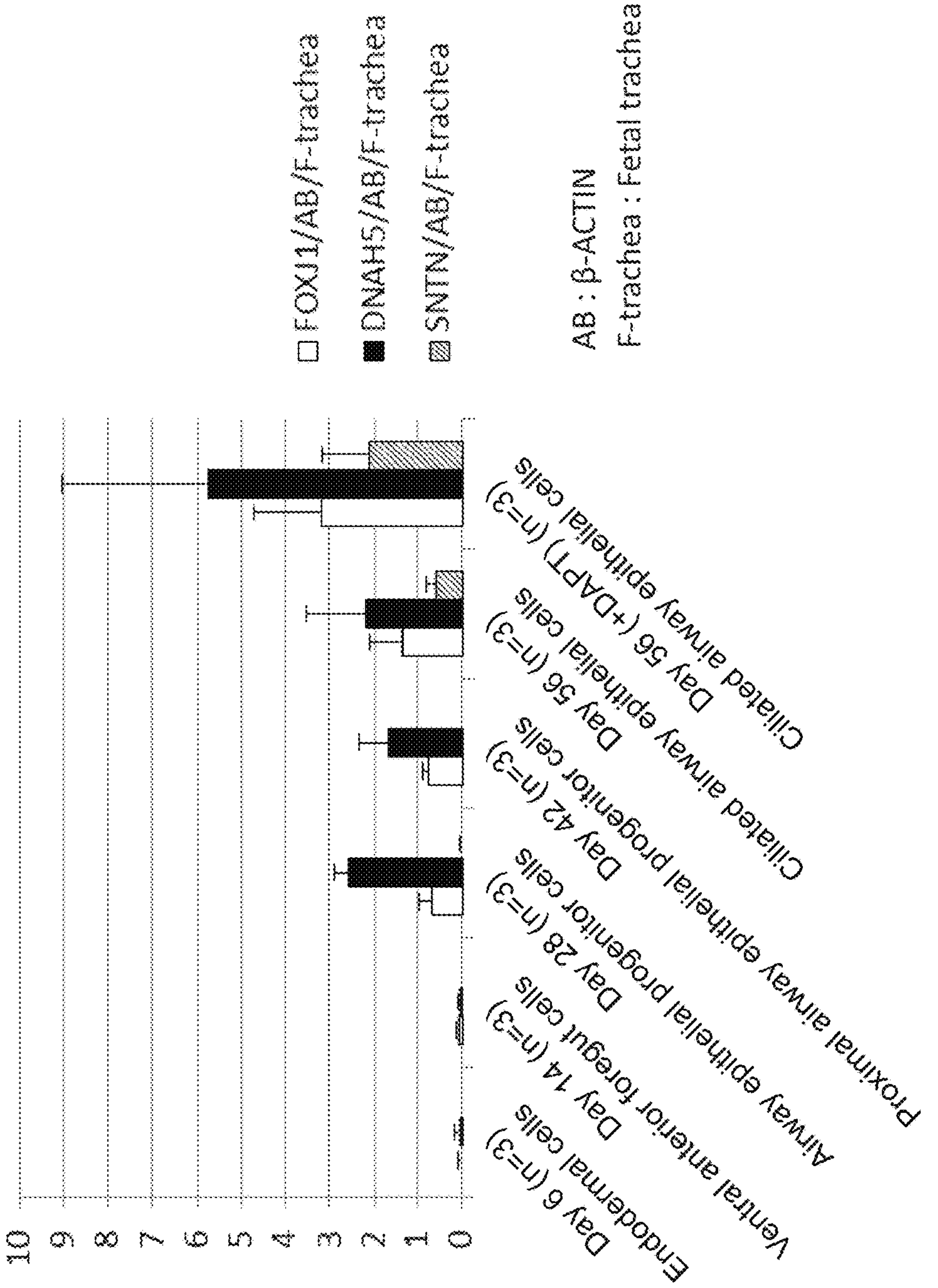
FIG. 8 shows the results of step-wise quantitative RT-PCR measurements of changes in expression levels of characteristic marker genes in the process in which ciliated airway epithelial cells are induced to differentiate with the use of human iPS cells (201B7).

FIG. 8 shows the results of step-wise quantitative RT-PCR measurements of changes in expression levels of characteristic marker genes in the process in which ciliated airway epithelial cells are induced to differentiate. On Day 6 (i.e., upon completion of Step 1), Day 14 (i.e., upon completion of Step 3), Day 28 (i.e., upon completion of Step 4), Day 42 (i.e., upon completion of Step 5), and Day 56 (i.e., upon completion of Step 6), expression levels of FOXJ1, DNAHS, and SNTN as marker genes specific to ciliated airway epithelial cells were analyzed via quantitative RT-PCR. Day 56 (+DAPT) represents the results of culture conducted in the medium for Step 6 supplemented with 10 μM DAPT from Day 42 (i.e., upon completion of Step 5). The measured values indicate the ratio of the cell expression levels to the amount of β-actin (AB) corrected with the expression levels in the human fetal trachea (F-trachea, 29-weeks pregnant, BioChain Institute).

As shown in FIG. 8, differentiation into ciliated airway epithelial cells was further accelerated in the medium for Step 6 supplemented with 10 μM DAPT (Wako) as a NOTCH signal inhibitor, and it was confirmed by subjecting FOXJ1, DNAHS, and SNTN to qRT-PCR.

It was possible to induce the ventral anterior foregut cells to differentiate into ciliated airway epithelial cells when the ventral anterior foregut cells were subjected to Step 5 and Step 6 without Step 4 after the ventral anterior foregut cells were isolated on Day 14 (i.e., upon completion of Step 3). In addition, the cell differentiation was achieved even if the period of Step 5 was 14 to 28 days and the period of Step 6 was 14 to 28 days.

In addition, FIG. 9A shows that airway epithelial cells other than the ciliated airway epithelial cells were also induced to differentiate on Day 56 with the use of human iPS cells (201B7) in the medium for Step 6 that was not supplemented with DAPT. Specifically, FIG. 9A shows immunostained images of SCGB1A1 indicating the Club cell, KRTS indicating the basal airway epithelial cell, and MUCSAC indicating the airway mucin-producing cell.

FIG. 9B is a continuation from FIG. 9A, which demonstrates that SCGB1A1, KRTS, and FOXJ1 as the ciliated airway epithelial cell were not expressed in the same cell.

Figure 9:
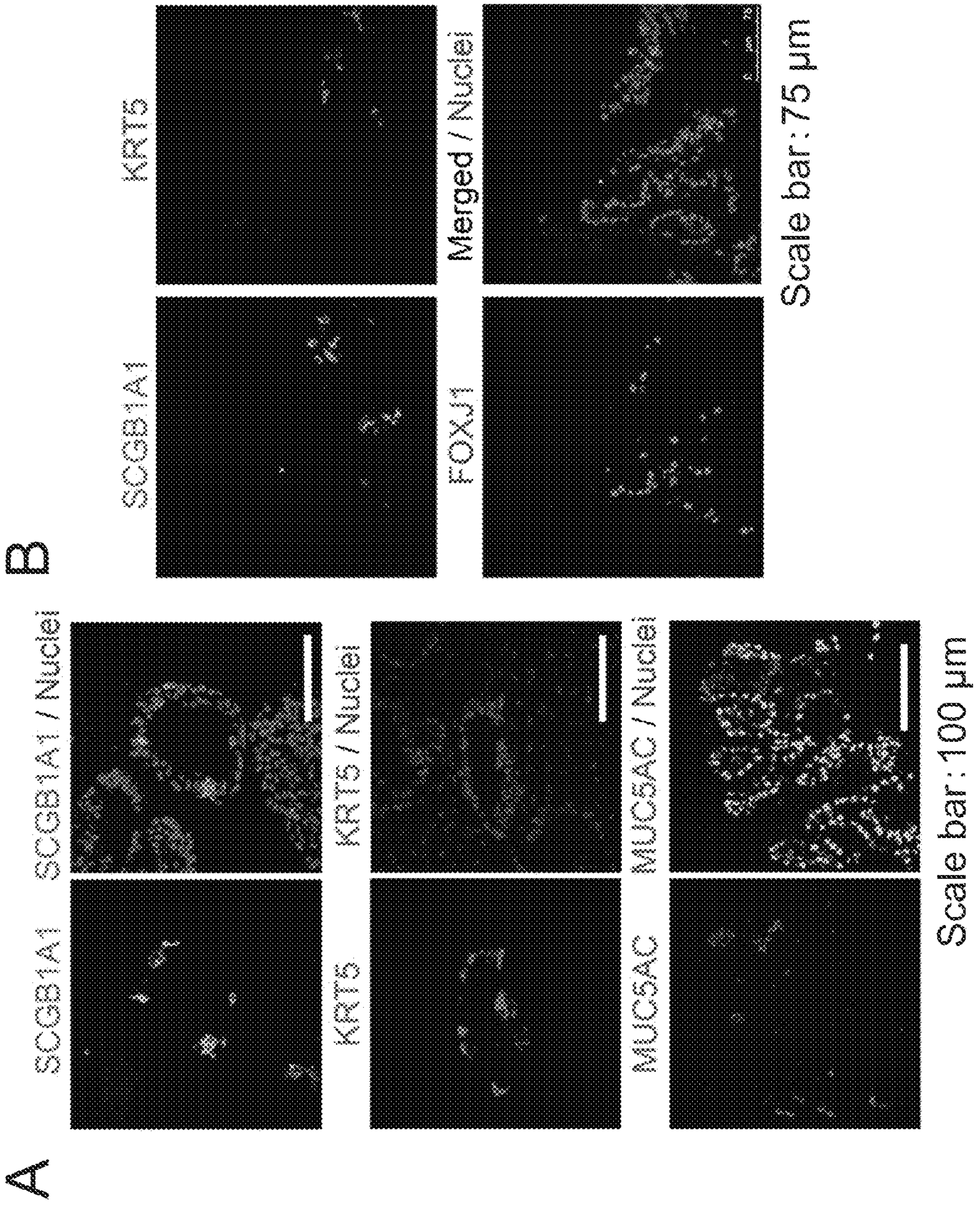
FIG. 9 shows the results of induction of differentiation with the use of human iPS cells (201B7) without the addition of DAPT to the medium for Step 6 demonstrating that airway epithelial cells other than the ciliated airway epithelial cells were induced to differentiate on Day 56.

The results shown in FIG. 9 demonstrate that, in addition to ciliated airway epithelial cells, airway epithelial cells, such as Club cells, basal airway epithelial cells, and airway mucin-producing cells, are also induced to differentiate when DAPT is not added to the medium for Step 6.

INDUSTRIAL APPLICABILITY

According to the present invention, airway epithelial cells can be efficiently produced from pluripotent stem cells.

All publications, patents, and patent applications cited herein are incorporated herein by reference in their entirety.

The invention claimed is:

1. A method for producing airway epithelial cells from mammalian pluripotent stem cells comprising Steps (1) to (6) below:

(1) culturing mammalian pluripotent stem cells in a medium containing activin A and a GSK3β inhibitor;

(2) culturing the cells obtained in Step (1) in a medium containing a BMP inhibitor and a TGFβ inhibitor;

(3) culturing the cells obtained in Step (2) in a medium containing BMP4, retinoic acid, and a GSK3β inhibitor to obtain ventral anterior foregut cells;

(4) optionally culturing the ventral anterior foregut cells obtained in Step (3) in a medium containing a GSK3β inhibitor and FGF10 to induce the cells to differentiate into airway epithelial progenitor cells;

(5) subjecting the ventral anterior foregut cells obtained in Step (3) or the airway epithelial progenitor cells obtained in Step (4) to three-dimensional culture in a medium containing a GSK3β inhibitor, FGF10, and a ROCK inhibitor to obtain proximal airway epithelial progenitor cells; and (6) subjecting the proximal airway epithelial progenitor cells obtained in Step (5) to three-dimensional culture in a medium containing a ROCK inhibitor but not containing a GSK3β inhibitor, thereby producing airway epithelial cells;

wherein the airway epithelial cells are selected from the group consisting of ciliated airway epithelial cells, airway mucin-producing cells, basal airway epithelial cells, and Club cells.

2. The method according to claim 1, wherein the GSK3β inhibitor is CHIR99021, the BMP inhibitor is Noggin, the TGFβ inhibitor is SB431542 and the ROCK inhibitor is Y-27632.

3. The method according to claim 1, wherein Step (1) comprises culturing mammalian pluripotent stem cells in a medium further supplemented with a ROCK inhibitor and/or an HDAC inhibitor.

4. The method according to claim 3, wherein the ROCK inhibitor is Y-27632 and/or the HDAC inhibitor is sodium butyrate.

5. The method according to claim 1, which further comprises, following Step (3), a step of concentrating ventral anterior foregut cells by isolating carboxypeptidase M (CPM)-positive cells.

6. The method according to claim 1, wherein Step (4) comprises subjecting ventral anterior foregut cells to culture in a medium further supplemented with a ROCK inhibitor.

7. The method according to claim 6, wherein the ROCK inhibitor is Y-27632.

8. The method according to claim 1, wherein, in Step (6), proximal airway epithelial progenitor cells are subjected to three-dimensional culture in a medium further supplemented with a NOTCH signal inhibitor and the resulting airway epithelial cells are ciliated airway epithelial cells.

9. The method according to claim 8, wherein the NOTCH signal inhibitor is DAPT.

10. The method according to claim 1, which further comprises, following Step (6), a step of isolating cells positive for one or more ciliated airway epithelial cell markers selected from the group consisting of Sentan (SNTN), FOXJ1, and DNAH5 as ciliated airway epithelial cells.

* * * * *